United States Patent
Mosmann et al.

(10) Patent No.: US 6,207,154 B1
(45) Date of Patent: *Mar. 27, 2001

(54) METHODS OF TREATMENT USING ANTAGONISTS OF CYTOKINE SYNTHESIS INHIBITORY FACTOR

(75) Inventors: Timothy R. Mosmann, Pittsford, NY (US); Kevin W. Moore; Martha W. Bond, both of Palo Alto, CA (US); Paulo J. M. Vieira, Carnaxide (PT)

(73) Assignee: Schering Corporation, Kenilworth, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 08/467,374

(22) Filed: Jun. 6, 1995

Related U.S. Application Data

(62) Division of application No. 08/248,564, filed on May 24, 1994, now abandoned, which is a continuation of application No. 07/904,124, filed on Jun. 25, 1992, now abandoned, which is a division of application No. 07/546,235, filed on Jun. 29, 1990, now abandoned.

(51) Int. Cl.[7] .................................................. A61K 39/395

(52) U.S. Cl. .................................... 424/139.1; 424/130.1; 424/141.1; 424/145.1; 424/184.1; 424/198.1

(58) Field of Search ............................... 424/145.1, 85.2, 424/85.1, 158.1, 198.1, 130.1, 139.1, 141.1, 184.1

(56) References Cited

U.S. PATENT DOCUMENTS 5,837,232  11/1998  De Waal Malefyt et al. ..... 424/85.2

OTHER PUBLICATIONS

Smith et al. J. of Immunology 131(4):1808–1815, Oct. 1983.*
Salgaller et al. Cancer Immunol. Immunotherapy 39:105–116, 1994.*
Burgess et al. J. Cell Biology 111:2129–38, Nov. 1990.*
Kumar et al. PNAS 87:1337–1341, Feb. 1990.*
R. Baer, et al., "DNA sequence and expression of the B95–8 Epstein–Barr virus genome," *Nature,* vol. 310, pp. 207–211, 1984.
D.J. Cher, et al., "Two Types of Murine Helper T Cell Clone. II. Delayed–Type Hypersensitivity is Mediated by T$_H$1 Clones," *J. of Immunol.,* vol. 138, pp. 3688–3694, Jun. 1987.
G.D. Demetri, et al., "Expression of ras Oncogenes in Cultured Human Cells Alters the Transcriptional and Post-transcriptional Regulation of Cytokine Genes," *J. Clin. Invent.,* vol. 86, pp. 1261–1269, Oct. 1990.
D.F. Fiorentino, et al., "Two Types of Mouse T Helper Cell. IV. Th2 Clones Secrete a Factor That Inhibits Cytokine Production by Th1 Clones," *J. Exp. Med.,* vol. 170, pp. 2081–2095, Dec. 1989.

B.V. Jegasothy, et al., "Immuno–Suppressive Lymphocyte Factors—III. Complete Purification and Partial Characterization of Human Inhibitor of DNA Synthesis," *Mol. Immunol.,* vol. 18, No. 5, pp. 395–041, 1981.
B.H. van Leeuwen, et al., "Molecular Organization of the Cytokine Gene Cluster, Involving the Human IL–3, IL–4, IL–5, and GM–CSF Genes, on Human Chromosome 5," *Blood,* vol. 73, No. 5, pp. 1142–1148, 1989.
R. Lewin, "Do Animals Read Minds, Tell Lies?" *Science,* vol. 238, p. 1350–1351, 1987.
F.Y. Liew, "Functional Heterogeneity of CD4+ T Cells in Leishmaniasis," *Immunology Today,* vol. 10, pp. 40–45, Feb. 1989.
K. Moore, et al., "Molecular Biology of Mouse and Human Cytokine Synthesis Inhibitory Factor (CSIF;IL–10)," *Cytokines: Basic Principles and Clinical Applications,* Congress Palace, Florence, Italy, pp. 1–8, Mar. 26–28, 1990.
T.R. Mosmann, et al., "Th1 and Th2 Cells: Different Patterns of Lymphokine Secretion Lead to Different Functional Properties," *Ann. Rev. Immunol.,* vol. 7, pp. 145–173, 1989.
T.R. Mosmann, et al., "Two Types of Mouse Helper T–Cell Clones," *Immunology Today,* vol. 8, Nos. 7 and 8, 1987.
T.R. Mosmann, et al., "Heterogeneity of Mouse Helper T Cells and Cross–Regulation of Th1 and Th2 Clones," *Progress Immunology,* Proceedings of the 7th International Congress of Immunology, vol. VII, pp. 611–618, Berlin, 1989.
C.R. Parish, "The Relationship Between Humoral and Cell–Mediated Immunity," *Transplant. Rev.,* vol. 13, pp. 35–66, 1972.
G.R. Reeck, et al., "'Homonolgy' in Proteins and Nucleic Acids: A Terminology Muddle and a Way out of it," *Cell,* vol. 50, p. 667, Aug. 28, 1987.
T. Yokota, et al., "Strategies for Cloning Mouse and Human Lymphokine Genes Using a Mammalian cDNA Expression Vector," *Lymphokines,* vol. 13, pp. 1–19.
Baer, et al., *Nature,* vol. 380, pp. 207–211, 1984.
Cher, et al., "Two Types of Murine Helper T Cell Clone. II. Delayed–Type Hypersensitivity is Mediated by T$_H$1 Clones," *J. of Immunol.,* vol. 138, pp. 3688–3694, Jun. 1987.

(List continued on next page.)

*Primary Examiner*—Prema Mertz
(74) *Attorney, Agent, or Firm*—David B. Schram; Cynthia Lee Foulke

(57) ABSTRACT

Mammalian genes and proteins, designated cytokine synthesis inhibitory factors (CSIFs, now known as Interleukin-10 (IL-10)), are provided which are capable of inhibiting the synthesis of cytokines associated with delayed type hypersensitivity responses, and which, together with antagonists, are useful in treating diseases associated with cytokine imbalances, such as leishmaniasis and other parasitic infections, and certain immune disorders including MHC associated autoimmune diseases caused by excessive production of interferon-$\gamma$.

9 Claims, 6 Drawing Sheets

OTHER PUBLICATIONS

Demetri, et al., *J. Clin. Invent.,* vol. 86, pp. 1261–1269, 1990.

D. F. Fiorentino, et al., "Two Types of Mouse T Helper Cell. IV. Th2 Clones Secrete a Factor That Inhibits Cytokine Production by Th1 Clones," *J. Exp. Med.,* vol. 170, pp. 2081–2095, Dec. 1989.

Jegasothy, et al., *Mol. Immunol.,* vol. 18, No. 5, pp. 395–401, 1981.

*J. Fed. Am. Soc. Exp. Biol.,* vol. 4, No. 7, 1990, Meeting of the American Society of Biochemistry and Molecular Biology, and the American Association of Immunologists, New Orleans, Jun. 4–7, 1990, p. 2191, abstract 2870; p. 2172, abstract 2764; p. 1742, abstract 279; p. 1734, abstract 233; p. 1705, abstract 60.

Leeumen, et al., *Blood,* vol. 73, No. 5, pp. 1142–1148, 1989.

Lewin, *Science,* vol. 237, p. 1350, 1987.

F. Y. Liew, "Functional Heterogeneity of CD4+ T Cells in Leishmaniasis," *Immunology Today,* vol. 10, pp. 40–45, Feb. 1989.

Kevin Moore, et al., "Molecular Biology of Mouse and Human Cytokine Synthesis Inhibitory Factor (CSI-F;IL–10)," *Cytokines: Basic Principles and Clinical Applications,* Congress Palace, Florence, Italy, pp. 1–8, Mar. 26–28, 1990.

Moore, et al., *Science,* vol. 248, pp. 1230–1234, 1990.

Mosmann, et al., "Th1 and Th2 Cells: Different Patterns of Lymphokine Secretion Lead to Different Functional Properties," *Ann. Rev. Immunol.,* vol. 7, pp. 145–173, 1989.

Mosmann, et al., "Two Types of Mouse Helper T–Cell Clones," *Immunology Today,* vol. 8, Nos. 7, and 8, 1987.

T. R. Mosmann, et al., "Heterogeneity of Mouse Helper T Cells and Cross–Regulation of Th1 and Th2 Clones," *Progress in Immunology,* Proceedings of the 7th International Congress of Immunology, vol. VII, pp. 611–618, Berlin, 1989.

C. R. Parish, "The Relationship Between Humoral and Cell–Mediated Immunity," *Transplant. Rev.,* vol. 13, pp. 35–66, 1972.

Reech, et al., *Cell,* vol. 50, p. 667, 1987.

P. Vieira, et al., "Isolation and Expression of Human Cytokine Synthesis Inhibitory Factor cDNA Clones: Homology to Epstein–Barr Virus Open Reading Frame BCRFI," *Proc. Natl. Acad. Sci. USA,* vol. 88, pp. 1172–1176, Feb. 1991.

Takashi Yokota, et al., "Strategies for Cloning Mouse and Human Lymphokine Genes Using a Mammalian cDNA Expression Vector," *Lymphokines,* vol. 13, pp. 1–19.

\* cited by examiner

```
                              29                                      56
AAA CCA CAA GAC AGA CTT GAA AAA GAA GGC ATG CAC AGC TCA GCA CTG CTC TGT
                                    MET His Ser Ser Ala Leu Leu Cys 83                                     110
TGC CTG GTC CTC CTG ACT GGG GTG AGG GCC AGC CCA GGC CAG GGC ACC CAG TCT
Cys Leu Val Leu Leu Thr Gly Val Arg Ala Ser Pro Gly Gln Gly Thr Gln Ser 137                                     164
GAG AAC AGC TGC ACC CAC TTC CCA GGC AAC CTG CCT AAC ATG CTT CGA GAT CTC
Glu Asn Ser Cys Thr His Pbe Pro Gly Asn Leu Pro Asn MET Leu Arg Asp Leu 191                                     218
CGA GAT GCC TTC AGC AGA GTG AAG ACT TTC TTT CAA ATG AAG GAT CAG CTG GAC
Arg Asp Ala Phe Ser Arg Val Lys Thr Phe Phe Gln MET Lys Asp Gln Leu Asp 245                                     272
AAC TTG TTG TTA AAG GAG TCC TTG CTG GAG GAC TTT AAG GGT TAC CTG GGT TGC
Asn Leu Leu Leu Lys Glu Ser Leu Leu Glu Asp Phe Lys Gly Tyr Leu Gly Cys 299                                     326
CAA GCC TTG TCT GAG ATG ATC CAG TTT TAC CTG GAG GAG GTG ATG CCC CAA GCT
Gln Ala Leu Ser Glu MET Ile Gln Phe Tyr Leu Glu Glu Val MET Pro Gln Ala 353                                     380
GAG AAC CAA GAC CCA GAC ATC AAG GCG CAT GTG AAC TCC CTG GGG GAG AAC CTG
Glu Asn Gln Asp Pro Asp Ile Lys Ala His Val Asn Ser Leu Gly Glu Asn Leu 407                                     434
AAG ACC CTC AGG CTG AGG CTA CGG CGC TGT CAT CGA TTT CTT CCC TGT GAA AAC
Lys Thr Leu Arg Leu Arg Leu Arg Arg Cys His Arg Phe Leu Pro Cys Glu Asn 461                                     488
AAG AGC AAG GCC GTG GAG CAG GTG AAG AAT GCC TTT AAT AAG CTC CAA GAG AAA
Lys Ser Lys Ala Val Glu Gln Val Lys Asn Ala Phe Asn Lys Leu Gln Glu Lys 515                                     542
GGC ATC TAC AAA GCC ATG AGT GAG TTT GAC ATC TTC ATC AAC TAC ATA GAA GCC
Gly Ile Tyr Lys Ala MET Ser Glu Phe Asp Ile Phe Ile Asn Tyr Ile Glu Ala 569                                     596
TAC ATG ACA ATG AAG ATA CGA AAC TGA GAC ATC AGG GTG GCG ACT CTA TAG ACT
Tyr MET Thr MET Lys Ile Arg Asn 623                                     650
CTA GGA CAT AAA TTA GAG GTC TCC AAA ATC GGA TCT GGG GCT CTG GGA TAG CTG
```

FIG. 4A

```
                                    677                                    704
ACC CAG CCC CTT GAG AAA CCT TAT TGT ACC TCT CTT ATA GAA TAT TTA TTA CCT 731                                    758
CTG ATA CCT CAA CCC CCA TTT CTA TTT ATT TAC TGA GCT TCT CTG TGA ACG ATT 785                                    812
TAG AAA GAA GCC CAA TAT TAT AAT TTT TTT CAA TAT TTA TTA TTT TCA CCT GTT 839                                    866
TTT AAG CTG TTT CCA TAG GGT GAC ACA CTA TGG TAT TTG AGT GTT TTA AGA TAA 893                                    920
ATT ATA AGT TAC ATA AGG GAG GAA AAA AAA TGT TCT TTG GGG AGC CAA CAG AAG 947                                    974
CTT CCA TTC CAA GCC TGA CCA CGC TTT CTA GCT GTT GAG CTG TTT TCC CTG ACC 1001                                   1028
TCC CTC TAA TTT ATC TTG TCT CTG GGC TTG GGG CTT CCT AAC TGC TAC AAA TAC 1055                                   1082
TCT TAG GAA GAG AAA CCA GGG AGC CCC TTT GAT GAT TAA TTC ACC TTC CAG TGT 1109                                   1136
CTC GGA GGG ATT CCC CTA ACC TCA TTC CCC AAC CAC TTC ATT CTT GAA AGC TGT 1163                                   1190
GGC CAG CTT GTT ATT TAT AAC AAC CTA AAT TTG GTT CTA GGC CGG GCG CGG TGG 1217                                   1244
CTC ACG CCT GTA ATC CCA GCA CTT TGG GAG GCT GAG GCG GGT GGA TCA CTT GAG 1271                                   1298
GTC AGG AGT TCC TAA CCA GCC TGG TCA ACA TGG TGA AAC CCC GTC TCT ACT AAA
```

FIG. 4B

```
1325
AAT ACA AAA ATT AGC CGG GCA TGG CGC GCA CCT GTA ATC CCA GCT ACT TGG
                                                                    1352

1379
GAG GCT GAG GCA AGA GAA TTG CTT GAA CCC AGG AGA TGG AAG TTG CAG TGA GCT
                                                                        1406

1433
GAT ATC ATG CCC CTG TAC TCC AGC CTG GGT GAC AGA GCA AGA CTC TGT CTC AAA
                                                                        1460

1487
AAA ATA AAA ATA AAA ATA AAT TTG GTT CTA ATA GAA CTC AGT TTT AAC TAG AAT
                                                                        1514

1541
TTA TTC AAT TCC TCT GGG AAT GTT ACA TTG TTT GTC TGT CTT CAT AGC AGA TTT
                                                                        1568

1595
TAA TTT TGA ATA AAT AAA TGT ATC TTA TTC ACA TCA AAA AAA AAA AAA AAA A
```

FIG. 4C

METHODS OF TREATMENT USING ANTAGONISTS OF CYTOKINE SYNTHESIS INHIBITORY FACTOR

CROSS-REFERENCE TO RELATED APPLICATIONS

This application is a divisional of application Ser. No. 08/248,564, filed May 24, 1994 now abandoned which is a continuation of application Ser. No. 07/904,124, filed Jun. 25, 1992 and now abandoned, which is a divisional of application Ser. No. 07/546,235, filed Jun. 29, 1990 and now abandoned.

FIELD OF THE INVENTION

The invention relates generally to methods and compositions for treating diseases associated with immune system imbalances, particularly imbalances involving humoral and cell-mediated immune responses. The invention also includes proteins and antagonists thereof capable of modulating the synthesis of certain cytokines involved in immune system to achieve therapeutic effects.

BACKGROUND

Immune responses to antigen are classified as being predominantly either cell-mediated, exemplified by the phenomena of delayed-type hypersensitivity (DTH), or humoral, exemplified by the production of antibodies. Cell-mediated immunity is of paramount importance for the rejection of tumors and for recovery from many viral, bacterial, protozoan, and fungal infections. In contrast, a humoral immune response is the most effective form of immunity for eliminating toxins and invading organisms from circulation. It has been observed that for different antigens one or the other of these two responses often predominates in a mutually exclusive fashion, and that the severity of some diseases, e.g. leprosy, leishmaniasis, and some types of autoimmunity, may be due the inappropriate dominance of one class of response over the other, Mosmann et al, Immunol. Today, Vol 8, pgs. 223–227 (1987); Mosmann et al, Ann. Rev. Immunol., Vol. 7, pgs. 145–173 (1989); Parish, Transplant. Rev, Vol. 13, pgs. 35–66 (1972); and Liew, Immunol. Today, Vol. 10, pgs. 40–45 (1989). It has further been observed that sets of cytokines are separately associated with DTH reactions and humoral immune responses, Cher et al, J. Immunol., Vol. 138, pgs. 3688–3694 (1987); and Mosmann et al (1987 and 1989, cited above), and it is thought that diseases associated with these classes of response are caused by the inappropriate production of the associated sets of cytokines.

For example, a large body of evidence suggests that excessive production of gamma interferon (IFN-$\gamma$) is responsible for major histocompatibility complex (MHC) associated autoimmune diseases: Hooks et al, New England J. Med., Vol. 301, pgs. 5–8 (1979) (elevated serum levels of IFN-$\gamma$ correlated with autoimmunity); Basham et al, J. Immunol., Vol. 130, pgs. 1492–1494 (1983) (IFN-$\gamma$ can increase MHC gene product expression); Battazzo et al, Lancet, pgs. 1115–1119 (Nov. 12, 1983) (aberrant MHC gene product expression correlated with some forms of autoimmunity); Hooks et al, Ann. N.Y. Acad, Sci., Vol., pgs. 21–32 (1980) (higher IFN-$\gamma$ levels correlated to greater severity of disease in SLE patients, and histamine-release enhancing activity of interferon can be inhibited by anti-interferon sera); and Iwatani et al, J. Clin. Endocrin, and Metabol., Vol. 63, pgs. 695–708 (1986) (anti-IFN-$\gamma$ monoclonal antibody eliminated the ability of leucoagglutinin-stimulated T cells to induce HLA-DR expression). It is hypothesized that excess IFN-$\gamma$ causes the inappropriate expression of MHC gene products which, in turn, causes autoimmune reactions against the tissues whose cells are inappropriately expressing the MHC products and displaying autoantigens in the context of the products.

In the area of clinical parasitology, it has recently been observed that the levels of IFN-$\gamma$ and IL-2 are important factors in the progression and/or resolution of the protozoan infection, leishmaniasis. In particular, the presence of adequate levels of IFN-$\gamma$ appears to be essential for the activation of infected macrophages to eliminate intracellular amastigotes, Mauel and Behin, in Cohen et al, eds., Immunology of Parasitic Infections (Blackwell, London, 1982). And, in murine models of the disease, it has been shown that high levels of IFN-$\gamma$ and low levels of IL-4 are associated with resolution, whereas low levels of IFN-$\gamma$ and high levels of IL-4 are associated with progression of leishmaniasis, Heinzel et al, J. Exp. Med., Vol. 169, pgs. 59–72 (1989).

In view of the above, it would be advantageous to have available agents that could shift the dominance of one class of immune response to the other, and in particular that could suppress or increase the synthesis of IFN-$\gamma$ and/or other cytokines, respectively, as required for therapy. Such agents would be highly advantageous for treatment of diseases associated with inappropriate or inadequate immune responses, such as tissue rejection, leishmaniasis and other parasitic diseases, and MHC associated immune disorders including rheumatoid arthritis, systemic lupus erythematosus (SLE), myasthenia gravis, insulin-dependent diabetes mellitus, thyroiditis, and the like.

SUMMARY OF THE INVENTION

The present invention is directed to mammalian cytokine synthesis inhibitory factor (CSIF), CSIF analogs, CSIF peptides, and CSIF antagonists. It includes nucleic acids coding for polypeptides exhibiting CSIF activity, as well as the polypeptides themselves, their agonistic and/or antagonistic analogs, methods for their production, and methods of using them to treat disorders associated with cytokine imbalances, particularly those leading to an inappropriate class of immune response. The invention also includes the use of CSIF or its antagonists, alone or as vaccine adjuvants, to selectively induce a predominantly cell-mediated immune response or a predominantly humoral immune response, respectively. Preferably, antagonists of CSIF are derived from monoclonal antibodies capable of blocking the biological activity of CSIF. The nucleic acids of the invention are defined (1) by their homology to, or their ability to form detectable hybrids with, the cloned complementary DNA (cDNA) sequences disclosed herein, and (2) by functional assays for CSIF activity applied to the polypeptides encoded by the nucleic acids. As used herein, the term "CSIF activity" in reference to a protein or a polypeptide means that the protein or polypeptide is capable of inhibiting or substantially reducing the level of production of at least one of the following cytokines in the assays described below: IFN-$\gamma$, interleukin-2 (IL-2), lymphotoxin, interleukin-3 (IL-3), or granulocyte-macrophage colony stimulating factor (GM-CSF).

A preferred embodiment of the invention is a mature human CSIF of the open reading frame defined by the following amino acid sequence:

MHSSALLCCLVLLTGVRASPGQGTQSENSCTHFPGNLPNM-

LRDLRDAFSRVKTFFQMKDQLDNLLLKESLLEDFKGYLGC-

QALSEMIQFYLEEVMPQAENQDPDIKAHVNSLGENLKTLR-

LRLRRCHRFLPCENKSKAVEQVKNAFNKLQEKGIYKAMSE-

FDIFINYIEAYMTMKIRN wherein the standard one-letter symbols for L-amino acids are listed left to right starting from the N-terminal methionine. More preferably, the mature human CSIF is defined by the following amino acid sequence:

SPGQGTQSENSCTHFPGNLPNMLRDLRDAFSRVKTFFQMKDQLD-

NLLLKESLLEDFKGYLGCQALSEMIQFYLEEVMPQAENQDPDIKA-

HVNSLGENLKTLRLRLRRCHRFLPCENKSKAVEQVKNAFNKLQ-

EKGIYKAMSEFDIFINYIEAYMTMKIRN

The invention is based in part on the discovery and cloning of cDNAs which are capable of expressing proteins having CSIF activity. Accordingly, several such clones designated pcD(SRα)-F115 (carrying a mouse CSIF gene), and pH5C and pH15C (each carrying a human CSIF gene) have been deposited with the American Type Culture Collection (ATCC), Rockville, Md. under the accession numbers 68027, 68191, and 68192, respectively.

BRIEF DESCRIPTION OF THE FIGURES

FIG. 4 illustrates the nucleotide sequence of the cDNA insert of pH15C.

DETAILED DESCRIPTION OF THE INVENTION

Figure 1:
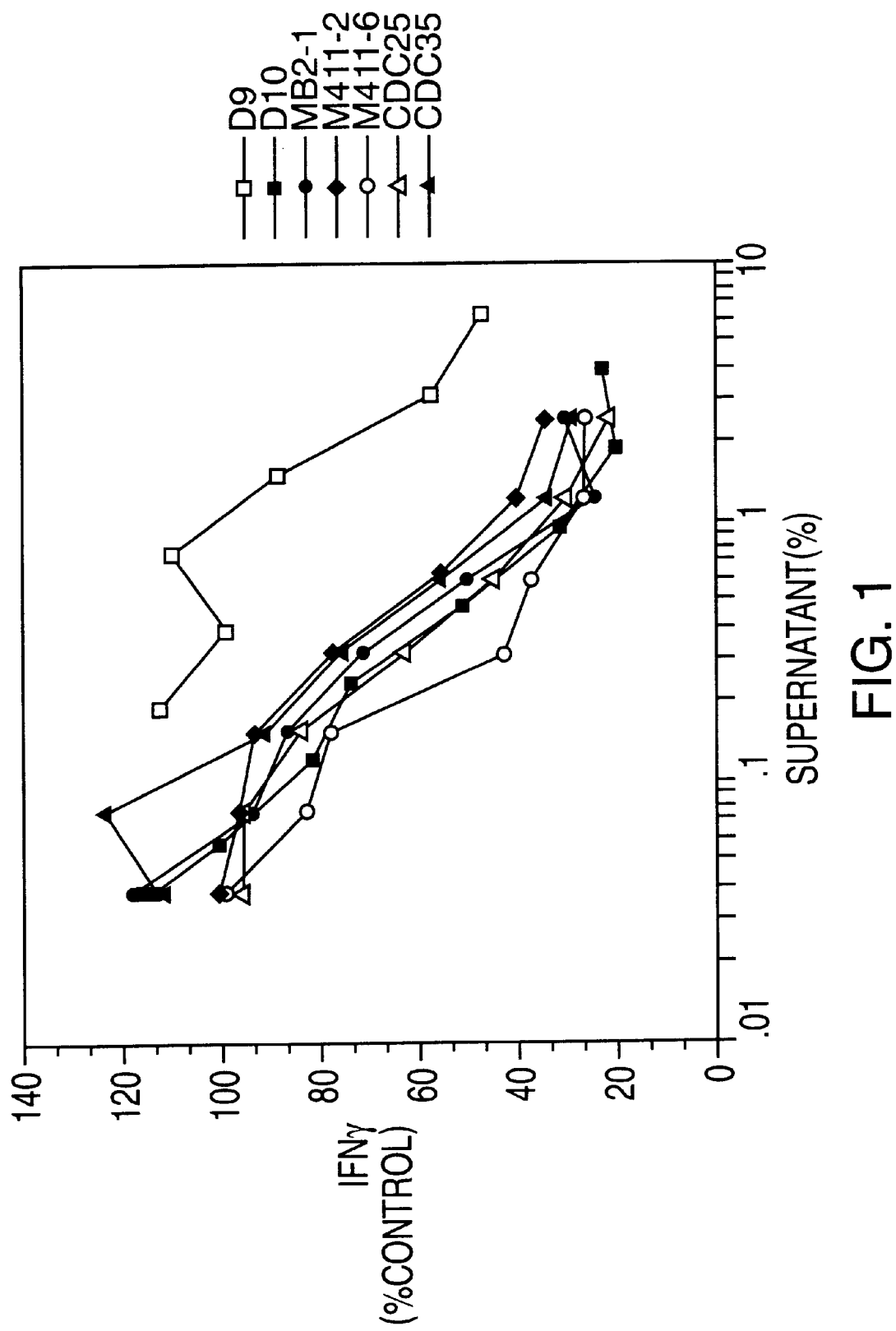
FIG. 1 illustrates a dose-response relationship for the degree of IFN-$_\gamma$ synthesis inhibition in several mouse T cell clones treated with different amounts of CSIF.
Figure 2:
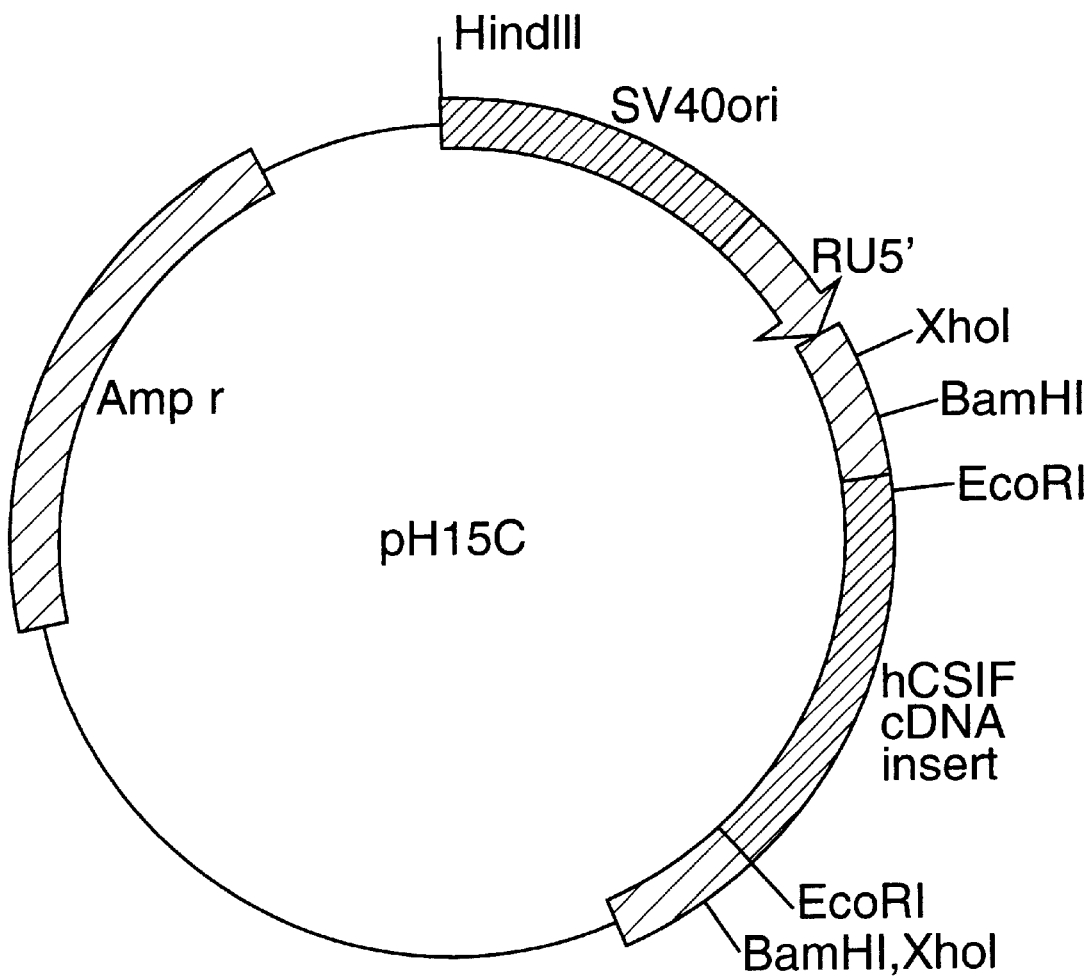
FIG. 2 is a diagram illustrating the major features of the mammalian expression vectors pH5C and pH15C.

The invention includes mature polypeptides, or proteins, of the largest open reading frames of the cDNA inserts of pH5C, pH15C, pcD(SRα)-F115, and effectively homologous cDNAs, as well as antagonists thereof. For secreted proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g. von Heijne, Nucleic Acids Research, Vol. 14, pgs. 4683–4690 (1986), and the precise amino acid composition of the signal peptide does not appear to be critical to its function, e.g. Randall et al, Science, Vol. 243, pgs. 1156–1159 (1989); Kaiser et al, Science, Vol. 235, pgs. 312–317 (1987). Consequently, mature proteins are readily expressed by vectors encoding signal peptides quite different than that encoded by the open reading frame defined by the cDNA inserts of pH5C, pH15C, and pcD(SRα)-F115.

I. Obtaining and Expressing CSIF cDNAs

The term "effectively homologous" as used herein means that the nucleotide sequence is capable of being detected by a hybridization probe derived from a cDNA clone of the invention. The exact numerical measure of homology necessary to detect nucleic acids coding for CSIF activity depends on several factors including (1) the homology of the probe to non-CSIF coding sequences associated with the target nucleic acids, (2) the stringency of the hybridization conditions, (3) whether single stranded or double stranded probes are employed, (4) whether RNA or DNA probes are employed, (5) the measures taken to reduce nonspecific binding of the probe, (6) the nature of the method used to label the probe, (7) the fraction of guanidine and cytosine bases in the probe, (8) the distribution of mismatches between probe and target, (9) the size of the probe, and the like. Preferably, an effectively homologous nucleic acid sequence is at least ninety percent (90%) homologous to the cDNA of the invention. Most particularly, an effectively homologous nucleic acid sequence is one whose cDNA can be isolated by a probe constructed from a cDNA insert of pcD(SRa)-F115, pH5C, pH15C, or an equivalent thereof, using the hybridization protocol described in the examples with no more than a few false positive signals, e.g. less than a hundred. There is an extensive literature that provides guidance in selecting conditions for such hybridizations, e.g. Hames et al, Nucleic Acid Hybridization: A Practical Approach (IRL Press, Washington, D.C., 1985); Gray et al, Proc. Natl. Acad. Sci., Vol. 80, pgs. 5842–5846 (1983); Kafatos et al, Nucleic Acids Research, Vol. 7, pgs. 1541–1552 (1979); Sambrook et al, Molecular Cloning: A Laboratory Manual, 2nd Ed. (Cold Spring Harbor Laboratory, New York, 1989); and Beltz et al, Meth. in Enzymol., Vol. 100, pgs. 266–285 (1983), to name a few.

Homology as the term is used herein is a measure of similarity between two nucleotide (or amino acid) sequences. Homology is expressed as the fraction or percentage of matching bases (or amino acids) after two sequences (possibly of unequal length) have been aligned. The term alignment is used in the sense defined by Sankoff and Kruskal in chapter one of Time Warps, String Edits, and Macromolecules: The Theory and Practice of Sequence Comparison (Addison-Wesley, Reading, Mass., 1983). Roughly, two sequences are aligned by maximizing the number of matching bases (or amino acids) between the two sequences with the insertion of a minimal number of "blank" or "null" bases into either sequence to bring about the maximum overlap. Given two sequences, algorithms are available for computing their homology, e.g. Needleham and Wunsch, J. Mol. Biol., Vol. 48, pgs. 443–453 (1970); and Sankoff and Kruskal (cited above) pgs. 23–29. Also, commercial services and software packages are available for performing such comparisons, e.g. Intelligenetics, Inc. (Palo Alto, Calif.); and University of Wisconsin Genetics Computer Group (Madison, Wis.).

Restriction endonuclease fragments of the vectors carrying the cDNAs of the invention are used to construct probes (using standard techniques such as nick-translation, e.g. see Sambrook et al., cited above) for screening at low hybridization stringencies genomic or cDNA libraries (again, constructed by standard techniques) of a cell type suspected of producing CSIF. Standard screening procedures are employed, e.g. Grunstein et al., Proc. Natl. Acad. Sci., Vol. 72, pgs. 3961–3965 (1975); or Benton et al., Science, Vol. 196, pgs. 180–183 (1977) or Woo, Methods in Enzymology, Vol. 68, pgs. 389–396 (1979). Alternatively, libraries can be screened with labeled oligonucleotide probes whose sequences are determined from the nucleotide sequences of the cDNA inserts of pcD(SRα)-F115, pH5C, and pH15C. Such probes can be synthesized on commercially available DNA synthesizers, e.g. Applied Biosystems model 381A, using standard techniques, e.g. Gait, Oligonucleotide Synthesis: A Practical Approach, (IRL Press, Washington D.C., 1984). In either case, it is preferable that the probe be at least 18–30 bases long. More preferably, the probe is at least 50–200 bases long. Hybridization probes can also be used to screen candidate sources of CSIF mRNA prior to library construction.

A wide range of single-cell and multicellular expression systems (i.e. host-expression vector combinations) can be used to produce the proteins of the invention. Possible types of host cells include, but are not limited to, bacterial, yeast, insect, mammalian, and the like. Many reviews are available which provide guidance for making choices and/or modifications of specific expression systems, e.g. to name a few, de Boer and Shepard, "Strategies for Optimizing Foreign Gene Expression in *Escherichia coli*," pgs. 205–247, in Kroon, ed. Genes: Structure and Expression (John Wiley & Sons, New York, 1983), review several *E. coli* expression systems; Kucherlapati et al., Critical Reviews in Biochemistry, Vol. 16, Issue 4, pgs. 349–379 (1984), and Banerji et al., Genetic Engineering, Vol. 5, pgs. 19–31 (1983) review methods for transfecting and transforming mammalian cells; Reznikoff and Gold, eds., Maximizing Gene Expression (Butterworths, Boston, 1986) review selected topics in gene expression in *E. coli*, yeast, and mammalian cells; and Thilly, Mammalian Cell Technology (Butterworths, Boston, 1986) reviews mammalian expression systems. Likewise, many reviews are available which describe techniques and conditions for linking and/or manipulating specific cDNAs and expression control sequences to create and/or modify expression vectors suitable for use with the present invention, e.g. Sambrook et al (cited above).

An *E. coli* expression system is disclosed by Riggs in U.S. Pat. No. 4,431,739, which is incorporated by reference. A particularly useful prokaryotic promoter for high expression in *E. coli* is the tac promoter, disclosed by de Boer in U.S. Pat. No. 4,551,433, which is incorporated herein by reference. Secretion expression vectors are also available for *E. coli* hosts. Particularly useful are the pIN-III-ompA vectors, disclosed by Ghrayeb et al., in EMBO J., Vol. 3, pgs. 2437–2442 (1984), in which the cDNA to be transcribed is fused to the portion of the *E. coli* OmpA gene encoding the signal peptide of the ompA protein which, in turn, causes the mature protein to be secreted into the periplasmic space of the bacteria. U.S. Pat. Nos. 4,336,336 and 4,338,397 also disclose secretion expression vectors for prokaryotes. Accordingly, these references are incorporated by reference.

Numerous stains of bacteria are suitable hosts for prokaryotic expression vectors including strains of *E. coli*, such as W3110 (ATCC No. 27325), JA221, C600, ED767, DH1, LE392, HB101, X1776 (ATCC No. 31244), X2282, RR1 (ATCC No. 31343) MRCI; strains of Bacillus subtilus; and other enterobacteriaceae such as Salmonella typhimurium or Serratia marcescens, and various species of Pseudomonas. General methods for deriving bacterial strains, such as *E. coli* K12 X1776, useful in the expression of eukaryotic proteins is disclosed by Curtis III in U.S. Pat. No. 4,190,495. Accordingly this patent is incorporated by reference.

In addition to prokaryotic and eukaryotic microorganisms, expression systems comprising cells derived from multicellular organism may also be used to produce proteins of the invention. Of particular interest are mammalian expression systems because their posttranslational processing machinery is more likely to produce biologically active mammalian proteins. Several DNA tumor viruses have been used as vectors for mammalian hosts. Particularly important are the numerous vectors which comprise SV40 replication, transcription, and/or translation control sequences coupled to bacterial replication control sequences, e.g. the pcD vectors developed by Okayama and Berg, disclosed in Mol. Cell. Biol., Vol. 2, pgs. 161–170 (1982) and Mol. Cell. Biol., Vol. 3, pgs. 280–289 (1983), and improved by Takebe et al, Mol. Cell. Biol., Vol. 8, pgs. 466–472 (1988). Accordingly, these references are incorporated herein by reference. Other SV40-based mammalian expression vectors include those disclosed by Kaufman and Sharp, in Mol. Cell. Biol., Vol. 2, pgs. 1304–1319 (1982), and Clark et al., in U.S. Pat. No. 4,675,285, both of which are incorporated herein by reference. Monkey cells are usually the preferred hosts for the above vectors. Such vectors containing the SV40 ori sequences and an intact A gene can replicate autonomously in monkey cells (to give higher copy numbers and/or more stable copy numbers than nonautonomously replicating plasmids). Moreover, vectors containing the SV40 ori sequences without an intact A gene can replicate autonomously to high copy numbers (but not stably) in COS7 monkey cells, described by Gluzman, Cell, Vol. 23, pgs. 175–182 (1981) and available from the ATCC (accession no. CRL 1651). The above SV40-based vectors are also capable of transforming other mammalian cells, such as mouse L cells, by integration into the host cell DNA.

Multicellular organisms can also serve as hosts for the production of CSIF, e.g. insect larvae, Maeda et al, Nature, Vol. 315, pgs. 592–594 (1985) and Ann. Rev. Entomol., pgs. 351–372 (1989); and transgenic animals, Jaenisch, Science, Vol. 240, pgs. 1468–1474 (1988).

II. In vitro Assays for CSIF

CSIF activity is the property of inhibiting the synthesis of at least one cytokine in the group consisting of IFN-$\gamma$, lymphotoxin, IL-2, IL-3, and GM-CSF in a population of T helper cells induced to synthesize one or more of these cytokines by exposure to syngeneic antigen presenting cells (APCs) and antigen. Preferably, the APCs are treated so that they are incapable of replication, but that their antigen processing machinery remains functional. This is conveniently accomplished by irradiating the APCs, e.g. with about 1500–3000 R (gamma or X-radiation) before mixing with the T cells.

Alternatively, cytokine inhibition may be assayed in primary or, preferably, secondary mixed lymphocyte reactions (MLR), in which case syngeneic APCs need not be used. MLRs are well known in the art, e.g. Bradley, pgs. 162–166, in Mishell et al, eds. *Selected Methods in Cellular Immunology* (Freeman, San Francisco, 1980); and Battisto et al, Meth. in Enzymol., Vol. 150, pgs. 83–91 (1987). Briefly, two populations of allogenic lymphoid cells are mixed, one of the populations having been treated prior to mixing to prevent proliferation, e.g. by irradiation. Preferably, the cell populations are prepared at a concentration of about $2 \times 10^6$ cells/ml in supplemented medium, e.g. RPMI 1640 with 10% fetal calf serum. For both controls and test cultures, mix 0.5 ml of each population for the assay. For a secondary MLR, the cells remaining after 7 days in the primary MLR are re-stimulated by freshly prepared, irradiated stimulator cells. The sample suspected of containing CSIF may be added to the test cultures at the time of mixing, and both controls and test cultures may be assayed for cytokine production from 1 to 3 days after mixing.

Obtaining T cell populations and/or APC populations for CSIF assays employs techniques well known in the art which are fully described in DiSabato et al, eds., Meth. in Enzymol., Vol. 108 (1984). APCs for the preferred CSIF assay are peripheral blood monocytes. These are obtained using standard techniques, e.g. as described by Boyum, Meth. in Enzymol., Vol. 108, pgs. 88–102 (1984); Mage, Meth. in Enzymol., Vol. 108, pgs. 118–132 (1984); Litvin et al., Meth. in Enzymol., Vol. 108, pgs. 298–302 (1984); Stevenson, Meth. in Enzymol., Vol. 108, pgs. 242–249 (1989); and Romain et al, Meth. in Enzymol., Vol. 108, pgs. 148–153 (1984), which references are incorporated by reference. Preferably, helper T cells are used in the CSIF assays, which are obtained by first separating lymphocytes from the peripheral blood then selecting, e.g. by panning or flow cytometry, helper cells using a commercially available anti-CD4 antibody, e.g. OKT4 described in U.S. Pat. No. 4,381,295 and available from Ortho Pharmaceutical Corp. The requisite techniques are fully disclosed in Boyum, Scand. J. Clin. Lab. Invest., Vol. 21 (Suppl. 97), pg. 77 (1968); Meth. in Enzymol., Vol. 108 (cited above), and in Bram et al, Meth. in Enzymol., Vol. 121, pgs. 737–748 (1986). Generally, PBLs are obtained from fresh blood by Ficoll-Hypaque density gradient centrifugation.

A variety of antigens can be employed in the assay, e.g. Keyhole limpet hemocyanin (KLH), fowl γ-globulin, or the like. More preferably, in place of antigen, helper T cells are stimulated with anti-CD3 monoclonal antibody, e.g. OKT3 disclosed in U.S. Pat. No. 4,361,549, in the assay.

Cytokine concentrations in control and test samples are measured by standard biological and/or immunochemical assays. Construction of immunochemical assays for specific cytokines is well known in the art when the purified cytokine is available, e. g. Campbell, Monoclonal Antibody Technology (Elsevier, Amsterdam, 1984); Tijssen, Practice and Theory of Enzyme Immunoassays (Elsevier, Amsterdam, 1985); and U.S. Pat. No. 4,486,530 are exemplary of the extensive literature on the subject. ELISA kits for human IL-2, human IL-3, and human GM-CSF are commercially available from Genzyme Corp. (Boston, Mass.); and an ELISA kit for human IFN-γ is commercially available from Endogen, Inc. (Boston, Mass.). Polyclonal antibodies specific for human lymphotoxin are available from Genzyme Corp. which can be used in a radioimmunoassay for human lymphotoxin, e.g. Chard, An Introduction to Radioimmunoassay and Related Techniques (Elsevier, Amsterdam, 1982).

Biological assays of the cytokines listed above can also be used to determine CSIF activity. A biological assay for human lymphotoxin is disclosed in Aggarwal, Meth. in Enzymol., Vol. 116, pgs. 441–447 (1985), and Matthews et al, pgs. 221–225, in Clemens et al, eds., Lymphokines and Interferons: A Practical Approach (IRL Press, Washington, D.C., 1987). Human IL-2 and GM-CSF can be assayed with factor dependent cell lines CTLL-2 and KG-1, available from the ATCC under accession numbers TIB 214 and CCL 246, respectively. Human IL-3 can be assayed by it ability to stimulate the formation of a wide range of hematopoietic cell colonies in soft agar cultures, e.g. as described by Metcalf, The Hemopoietic Colony Stimulating Factors (Elsevier, Amsterdam, 1984). INF-γ can be quantified with anti-viral assays, e.g. Meager, pgs. 129–147, in Clemens et al, eds. (cited above).

Cytokine production can also be determined by mRNA analysis. Cytokine mRNAs can be measured by cytoplasmic dot hybridization as described by White et al., J. Biol. Chem., Vol. 257, pgs. 8569–8572 (1982) and Gillespie et al., U.S. Pat. No. 4,483,920. Accordingly, these references are incorporated by reference. Other approaches include dot blotting using purified RNA, e.g. chapter 6, in Hames et al., eds., Nucleic Acid Hybridization A Practical Approach (IRL Press, Washington, D.C., 1985). Generally, cytoplasmic dot hybridization involves anchoring mRNA from a cell or tissue sample onto a solid phase support, e.g. nitrocellulose, hybridizing a DNA probe to the anchored mRNA, and removing probe sequences nonspecifically bound to the solid phase support or forming mismatched hybrids with the mRNA so that only probe sequences forming substantially perfect hybrids with target mRNAs remain. The amount of DNA probe remaining is a measure of the number of target mRNA anchored to the solid phase support. The amount of DNA probe remaining is determined by the signal generated by its label. Several standard techniques are available for labeling single and double stranded nucleic acid fragments. They include incorporation of radioactive labels, e.g. Harper et al., Chromosoma, Vol. 83, pgs. 431–439 (1984); direct attachment of fluorescent labels, e.g. Smith et al., Nucleic Acids Research, Vol. 13, pgs. 2399–2412 (1985), and Connolly et al., Nucleic Acids Research, Vol. 13, pgs. 4485–4502 (1985); and various chemical modifications of the nucleic acid fragments that render them detectable immunochemically or by other affinity reactions, e.g. Tchen et al., Proc. Natl. Acad. Sci., Vol. 81, pgs. 3466–3470 (1984); Richardson et al., Nucleic Acids Research, Vol. 11, pgs. 6167–6184 (1983); Langer et al., Proc. Natl. Acad. Sci., Vol. 78, pgs. 6633–6637 (1981); Brigati et al., Virology, Vol. 126, pgs. 32–50 (1983); Broker et al., Nucleic Acids Research, Vol. 5, pgs. 363–384 (1978); and Bayer et al., Methods of Biochemical Analysis, Vol. 26, pgs. 1–45 (1980).

Preferably mRNA from T cells is anchored for hybridization to the probe by the following protocol. Isolated T cells are lysed by suspending in a lysis buffer (0.14 M NaCl, 1.5 mM $MgCl_2$, 10 mM Tris-HCl pH 8.6, 0.5% Nonidet P-40 (a nonionic detergent, e.g. from Sigma)) at 4° C. at a final concentration of $1 \times 10^8$ cells/ml. The suspension is vortexed for 10 sec and the nuclei are pelleted (13,000 g, 2.5 min). The resulting cytoplasmic lysates are then transferred to a sterile 1.5 ml tube containing 0.3 volumes of 20×SSC (1×SSC=0.15 M NaCl, 0.015 M trisodium citrate (standard saline citrate)) and 0.2 volumes of 37% (w/w) formaldehyde. The mixture is then incubated at 60° C. for 15 min and stored in aliquots at −70° C. For analysis, 15 ml of each sample is titered by serial three fold dilutions in 15×SSC into a 96-well flat-bottomed microtiter plate (Falcon, Becton Dickinson, Oxnard, Calif.) in 0.1 ml. Each dilution is applied with suction to a sheet of Nytran (a modified nylon support available from Schleicher and Schuell, Keene, N.H.; 0.45 mm pore size) supported on a filter paper (Whatman 3 mm Chr, Whatman Inc., Clifton, N.J.) utilizing a 96 hold Minifold apparatus (Schleicher and Schuell). The Nytran paper is then baked (80° C., 2 H) and treated with a prehybridization solution consisting of 50% formamide (BRL, Gaithersburg, Md.) 6×SSC, 50 mg/ml *E. coli* tRNA (Sigma), 0.2% (w/v) each of ficoll (MW=400,000), polyvinylpyrollidone, and bovine serum albumin (BSA). The probe is applied to the Nytran support at a concentrate of about 50 ng probe/ml of prehybridization solution. Following hybridization, the support is washed two times for 15 min each at room temperature in 2×SSC, then twice for 30 min each at 60° C. in 2×SSC/0.5% SDS. The support is then exposed to film using an intensifying screen and quantitated by scanning with a laser densitometer (e.g. Ultroscan XL, LKB Instruments Inc., Gaithersburg, Md.). If cytoplasmic dot hybridization lacks sufficient sensitivity, preferably the RNA is first extracted from the PBLs prior to blotting. For example, RNA may be extracted by the guanidinium thiocyanate method disclosed by Chirgwin et al., in Biochemistry, Vol. 18, pgs. 5294–5299 (1979).

In some cases, samples to be tested for CSIF activity must be pretreated to remove predetermined cytokines that might interfere with the assay. For example, IL-2 increases the production of IFN-$_\gamma$ in some cells. Thus depending on the helper T cells used in the assay, IL-2 may have to be removed from the sample being tested. Such removals are conveniently accomplished by passing the sample over a standard anti-cytokine affinity column.

III. Monoclonal Antibodies and Antagonists Specific for CSIF

Preferably, antagonists of the invention are derived from antibodies specific for human CSIF. More preferably, the antagonists of the invention comprise fragments or binding compositions specific for human CSIF. Antibodies comprise an assembly of polypeptide chains linked together by disulfide bridges. Two major polypeptide chains, referred to as the light chain and the heavy chain, make up all major structural classes (isotypes) of antibody. Both heavy chains and light chains are further divided into subregions referred to as variable regions and constant regions. Heavy chains comprise a single variable region and three different constant regions, and light chains comprise a single variable region (different from that of the heavy chain) and a single constant region (different from those of the heavy chain). The variable regions of the heavy chain and light chain are responsible for the antibody's binding specificity.

As used herein, the term "heavy chain variable region" means a polypeptide (1) which is from 110 to 125 amino acids in length, and (2) whose amino acid sequence corresponds to that of a heavy chain of a monoclonal antibody of the invention, starting from the heavy chain's N-terminal amino acid. Likewise, the term "light chain variable region" means a polypeptide (1) which is from 95 to 115 amino acids in length, and (2) whose amino acid sequence corresponds to that of a light chain of a monoclonal antibody of the invention, starting from the light chain's N-terminal amino acid.

As used herein the term "monoclonal antibody" refers to homogeneous populations of immunoglobulins which are capable of specifically binding to human CSIF.

As used herein the term "binding composition" means a composition comprising two polypeptide chains (1) which, when operationally associated, assume a conformation having high binding affinity for human CSIF, and (2) which are derived from a hybridoma producing monoclonal antibodies specific for human CSIF. The term "operationally associated" is meant to indicate that the two polypeptide chains can be positioned relative to one another for binding by a variety of means, including by association in a native antibody fragment, such as Fab or Fv, or by way of genetically engineered cysteine-containing peptide linkers at the carboxyl termini. Normally, the two polypeptide chains correspond to the light chain variable region and heavy chain variable region of a monoclonal antibody specific for human CSIF. Preferably, antagonists of the invention are derived from monoclonal antibodies specific for human CSIF. Monoclonal antibodies capable of blocking, or neutralizing, CSIF are selected by their ability to inhibit CSIF-induced effects in standard CSIF bioassays, e.g. inhibition of IFN-$_\gamma$ synthesis.

Hybridomas of the invention are produced by well known techniques. Usually, the process involves the fusion of an immortalizing cell line with a B-lymphocyte which produces the desired antibody. Alternatively, non-fusion techniques for generating an immortal antibody producing cell lines are possible, and come within the purview of the present invention, e.g. virally induced transformation: Casali et al., "Human Monoclonals from Antigen-Specific Selection of B Lymphocytes and Transformation by EBV," Science, Vol. 234, pgs. 476–479 (1986). Immortalizing cell lines are usually transformed mammalian cells, particularly myeloma cells of rodent, bovine, and human origin. Most frequently, rat or mouse myeloma cell lines are employed as a matter of convenience and availability. Techniques for obtaining the appropriate lymphocytes from mammals injected with the target antigen are well known. Generally, either peripheral blood lymphocytes (PBLs) are used if cells of human origin are desired, or spleen cells or lymph node cells are used if non-human mammalian sources are desired. A host mammal is injected with repeated dosages of the purified antigen, and the mammal is permitted to generate the desired antibody producing cells before these are harvested for fusion with the immortalizing cell line. Techniques for fusion are also well known in the art, and in general, involve mixing the cells with a fusing agent, such as polyethylene glycol. Hybridomas are selected by standard procedures, such as HAT selection. From among these hybridomas, those secreting the desired antibody, i.e. specific for human CSIF, are selected by assaying their culture medium by standard immunoassays, such as Western blotting, ELISA, RIA, CSIF neutralizing capability, or the like. Antibodies are recovered from the medium using standard protein purification techniques, e.g. Tijssen, Practice and Theory of Enzyme Immunoassays (Elsevier, Amsterdam, 1985). Many references are available for guidance in applying any of the above techniques, e.g. Kohler et al., Hybridoma Techniques (Cold Spring Harbor Laboratory, New York, 1980); Tijssen, Practice and Theory of Enzyme Immunoassays (Elsevier, Amsterdam, 1985); Campbell, Monoclonal Antibody Technology (Elsevier, Amsterdam, 1984); Hurrell, Monoclonal Hybridoma Antibodies: Techniques and Applications (CRC Press, Boca Raton, Fla., 1982); and the like. Hybridomas producing monoclonal antibodies specific for human CSIF are then subjected to a second screen using the CSIF assays described above to select ones capable of blocking, or neutralizing, the biological activity of CSIF.

The use and generation of fragments of antibodies is also well known, e.g. Fab fragments: Tijssen, Practice and Theory of Enzyme Immunoassays (Elsevier, Amsterdam, 1985); and Fv fragments: Hochman et al. Biochemistry, Vol. 12, pgs. 1130–1135 (1973), Sharon et al., Biochemistry, Vol. 15, pgs. 1591–1594 (1976) and Ehrlich et al., U.S. Pat. No. 4,355,023; and antibody half molecules: Auditore-Hargreaves, U.S. Pat. No. 4,470,925.

Antibodies and antibody fragments characteristic of hybridomas of the invention can also be produced by recombinant means by extracting messenger RNA, constructing a cDNA library, and selecting clones which encode segments of the antibody molecule, e.g. Wall et al., Nucleic Acids Research, Vol. 5, pgs. 3113–3128 (1978); Zakut et al., Nucleic Acids Research, Vol. 8, pgs. 3591–3601 (1980); Cabilly et al., Proc. Natl. Acad. Sci., Vol. 81, pgs. 3273–3277 (1984); Boss et al., Nucleic Acids Research, Vol. 12, pgs. 3791–3806 (1984); Amster et al., Nucleic Acids Research, Vol. 8, pgs. 2055–2065 (1980); Moore et al., U.S. Pat. No. 4,642,334; Skerra et al, Science, Vol. 240, pgs. 1038–1041(1988); and Huse et al, Science, Vol. 246, pgs. 1275–1281 (1989). In particular, such techniques can be used to produce interspecific monoclonal antibodies, wherein the binding region of one species is combined with non-binding region of the antibody of another species to reduce immunogenicity, e.g. Liu et al., Proc. Natl. Acad. Sci., Vol. 84, pgs. 3439–3443 (1987).

IV. Purification and Pharmaceutical Compositions

When polypeptides of the present invention are expressed in soluble form, for example as a secreted product of transformed yeast or mammalian cells, they can be purified according to standard procedures of the art, including steps of ammonium sulfate precipitation, ion exchange chromatography, gel filtration, electrophoresis, affinity chromatography, and/or the like, e.g. "Enzyme Purification and Related Techniques," Methods in Enzymology, 22:233–577 (1977), and Scopes, R., Protein Purification: Principles and Practice (Springer-Verlag, New York, 1982) provide guidance in such purifications. Likewise, when polypeptides of the invention are expressed in insoluble form, for example as aggregates, inclusion bodies, or the like, they can be purified by standard procedures in the art, including separating the inclusion bodies from disrupted host cells by centrifugation, solublizing the inclusion bodies with chaotropic and reducing agents, diluting the solubilized mixture, and lowering the concentration of chaotropic agent and reducing agent so that the polypeptide takes on a biologically active conformation. The latter procedures are disclosed in the following references, which are incorporated by reference: Winkler et al, Biochemistry, 25: 4041–4045 (1986); Winkler et al, Biotechnology, 3: 992–998 (1985); Koths et al, U.S. Pat. No. 4,569,790; and European patent applications 86306917.5 and 86306353.3.

As used herein "effective amount" means an amount sufficient to ameliorate a symptom of an autoimmune condition. The effective amount for a particular patient may vary depending on such factors as the state of the autoimmune condition being treated, the overall health of the patient, method of administration, the severity of side-effects, and the like. Generally, CSIF is administered as a pharmaceutical composition comprising an effective amount of CSIF and a pharmaceutical carrier. A pharmaceutical carrier can be any compatible, non-toxic substance suitable for delivering the compositions of the invention to a patient. Generally, compositions useful for parenteral administration of such drugs are well known, e.g. Remington's Pharmaceutical Science, 15th Ed. (Mack Publishing Company, Easton, Pa. 1980). Alternatively, compositions of the invention may be introduced into a patient's body by implantable or injectable drug delivery system, e.g. Urquhart et al., Ann. Rev. Pharmacol. Toxicol., Vol. 24, pgs. 199–236 (1984); Lewis, ed. Controlled Release of Pesticides and Pharmaceuticals (Plenum Press, New York, 1981); U.S. Pat. No. 3,773,919; U.S. Pat. No. 3,270,960; and the like.

When administered parenterally, the CSIF is formulated in a unit dosage injectable form (solution, suspension, emulsion) in association with a pharmaceutical carrier. Examples of such carriers are normal saline, Ringer's solution, dextrose solution, and Hank's solution. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The CSIF is preferably formulated in purified form substantially free of aggregates and other proteins at a concentration in the range of about 5 to 20 $\mu$g/ml. Preferably, CSIF is administered by continuous infusion so that an amount in the range of about 50–800 $\mu$g is delivered per day (i.e. about 1–16 $\mu$g/kg/day). The daily infusion rate may be varied based on monitoring of side effects and blood cell counts.

CSIF can be purified from culture supernatants of mammalian cells transiently transfected or stably transformed by an expression vector carrying an CSIF gene. Preferably, CSIF is purified from culture supernatants of COS 7 cells transiently transfected by the pcD expression vector. Transfection of COS 7 cells with pcD proceeds as follows: One day prior to transfection, approximately $10^6$ COS 7 monkey cells are seeded onto individual 100 mm plates in Dulbecco's modified Eagle medium (DME) containing 10% fetal calf serum and 2 mM glutamine. To perform the transfection, the medium is aspirated from each plate and replaced with 4 ml of DME containing 50 mM Tris.HCl pH 7.4, 400 mg/ml DEAE-Dextran and 50 $\mu$g of plasmid DNA. The plates are incubated for four hours at 37° C., then the DNA-containing medium is removed, and the plates are washed twice with 5 ml of serum-free DME. DME is added back to the plates which are then incubated for an additional 3 hrs at 37° C. The plates are washed once with DME, after which DME containing 4% fetal calf serum, 2 mM glutamine, penicillin (100 U/L) and streptomycin (100 $\mu$g/L) at standard concentrations is added. The cells are then incubated for 72 hrs at 37° C., after which the growth medium is collected for purification of CSIF. Alternatively, transfection can be accomplished by electroporation as described in the examples. Plasmid DNA for the transfections is obtained by growing pcD(SR$\alpha$) containing the CSIF cDNA insert in *E. coli* MC1061, described by Casadaban and Cohen, J. Mol. Biol., Vol. 138, pgs. 179–207 (1980), or like organism. The plasmid DNA is isolated from the cultures by standard techniques, e.g. Maniatis et al., Molecular Cloning: A Laboratory Manual (Cold Spring Harbor Laboratory, New York, 1982).

When the antagonists of the inventions are derived from antibodies, they are normally administered parenterally, preferably intravenously. Since such protein or peptide antagonists may be immunogenic they are preferably administered slowly, either by a conventional IV administration set or from a subcutaneous depot, e.g. as taught by Tomasi et al, U.S. Pat. No. 4,732,863. When administered parenterally, the antibodies and/or fragments are formulated in a unit dosage injectable form in association with a pharmaceutical carrier, as described above. The antibody is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml.

Selecting an administration regimen for an antagonist depends on several factors, including the serum turnover rate of the antagonist, the serum level of CSIF associated with the disorder being treated, the immunogenicity of the antagonist, the accessibility of the target CSIF (e.g. if non-serum CSIF is to be blocked), the relative affinity of CSIF to its receptor(s) versus CSIF to the antagonist, and the like. Preferably, an administration regimen maximizes the amount of antagonist delivered to the patient consistent with an acceptable level of side effects. Accordingly, the amount of antagonist delivered depends in part on the particular antagonist and the severity of the condition being treated. Guidance in selecting appropriate doses is found in the literature on therapeutic uses of antibodies, e.g. Bach et al., chapter 22, in Ferrone et al., eds., Handbook of Monoclonal Antibodies (Noges Publications, Park Ridge, N.J., 1985); and Russell, pgs. 303–357, and Smith et al., pgs. 365–389, in Haber et al., eds. Antibodies in Human Diagnosis and Therapy (Raven Press, New York, 1977). Preferably, whenever the antagonist comprises monoclonal antibodies or Fab-sized fragments thereof (including binding compositions), the dose is in the range of about 1–20 mg/kg per day. More preferably the dose is in the range of about 1–10 mg/kg per day.

V. Genetically Engineered Mutant CSIFs

Once nucleic acid sequence and/or amino acid sequence information is available for a native protein a variety of techniques become available for producing virtually any mutation in the native sequence, e.g. Shortle, in Science, Vol. 229, pgs. 1193–1201 (1985); Zoller and Smith, Methods in Enzymology, Vol. 100, pgs. 468–500 (1983); Mark et al., U.S. Pat. No. 4,518,584; Wells et al., in Gene, Vol. 34, pgs. 315–323 (1985); Estell et al., Science, Vol. 233, pgs. 659–663 (1986); Mullenbach et 20 al., J. Biol. Chem., Vol. 261, pgs. 719–722 (1986), and Feretti et al., Proc. Natl. Acad. Sci., Vol. 83, pgs.. 597–603 (1986). Accordingly, these references are incorporated by reference.

Muteins of the natural polypeptide may be desirable in a variety of circumstances. For example, undesirable side effects might be reduced by certain muteins, particularly if the side effect activity is associated with a different part of the polypeptide from that of the desired activity. In some expression systems, the native polypeptide may be susceptible to degradation by proteases. In such cases, selected substitutions and/or deletions of amino acids which change the susceptible sequences can significantly enhance yields, e.g. British patent application 2173-804-A where Arg at position 275 of human tissue plasminogen activator is replaced by Gly or Glu. Muteins may also increase yields in purification procedures and/or increase shelf lives of proteins by eliminating amino acids susceptible to oxidation, acylation, alkylation, or other chemical modifications. For example, methionines readily undergo oxidation to form sulfoxides, which in many proteins is associated with loss of biological activity, e.g. Brot and Weissbach, Arch. Biochem. Biophys., Vol. 223, pg. 271 (1983). Often methionines can be replaced by more inert amino acids with little or no loss of biological activity, e.g. Australian patent application AU-A-52451/86. In bacterial expression systems, yields can sometimes be increased by eliminating or replacing conformationally inessential cystiene residues, e.g. Mark et al., U.S. Pat. No. 4,518,584.

Preferably cassette mutagenesis is employed to generate mutant proteins. A synthetic gene is constructed with a sequence of unique (when inserted in an appropriate vector) restriction endonuclease sites spaced approximately uniformly along the gene. The unique restriction sites allow segments of the gene to be conveniently excised and replaced with synthetic oligonucleotides (i.e. "cassettes") which code for desired mutations. Determination of the number and distribution of unique restriction sites entails the consideration of several factors including (1) preexisting restriction sites in the vector to be employed in expression, (2) whether species or genera-specific codon usage is desired, (3) the number of different non-vector-cutting restriction endonucleases available (and their multiplicities within the synthetic gene), and (4) the convenience and reliability of synthesizing and/or sequencing the segments between the unique restriction sites.

The above technique is a convenient way to effect conservative amino acid substitutions, and the like, in the native protein sequence. "Conservative" as used herein means (i) that the alterations are as conformationally neutral as possible, that is, designed to produce minimal changes in the tertiary structure of the mutant polypeptides as compared to the native protein, and (ii) that the alterations are as antigenically neutral as possible, that is, designed to produce minimal changes in the antigenic determinants of the mutant polypeptides as compared to the native protein. Conformational neutrality is desirable for preserving biological activity, and antigenic neutrality is desirable for avoiding the triggering of immunogenic responses in patients or animals treated with the compounds of the invention. While it is difficult to select with absolute certainty which alternatives will be conformationally and antigenically neutral, rules exist which can guide those skilled in the art to make alterations that have high probabilities of being conformationally and antigenically neutral, e.g. Anfisen (cited above); Berzofsky, Science, Vol. 229, pgs. 932–940 (1985); and Bowie et al, Science, Vol. 247, pgs. 1306–1310 (1990). Some of the more important rules include (1) substitution of hydrophobic residues are less likely to produce changes in antigenicity because they are likely to be located in the protein's interior, e.g. Berzofsky (cited above) and Bowie et al (cited above); (2) substitution of physiochemically similar, i.e. synonymous, residues are less likely to produce conformational changes because the replacement amino acid can play the same structural role as the substituted amino acid; and (3) alteration of evolutionarily conserved sequences is likely to produce deleterious conformational effects because evolutionary conservation suggests sequences may be functionally important. In addition to such basic rules for selecting mutein sequences, assays are available to confirm the biological activity and conformation of the engineered molecules. Biological assays for the polypeptides of the invention are described more fully above. Changes in conformation can be tested by at least two well known assays: the microcomplement fixation method, e.g. Wasserman et al., J. Immunol., Vol. 87, pgs. 290–295 (1961), or Levine et al. Methods in Enzymology, Vol. 11, pgs. 928–936 (1967) used widely in evolutionary studies of the tertiary structures of proteins; and affinities to sets of conformation-specific monoclonal antibodies, e.g. Lewis et al., Biochemistry, Vol 22, pgs. 948–954 (1983).

VI. Human CSIF Peptide Antibodies

The invention includes peptides derived from human CSIF, and immunogens comprising conjugates between carriers and peptides of the invention. The term immunogen as used herein refers to a substance which is capable of causing an immune response. The term carrier as used herein refers to any substance which when chemically conjugated to a peptide of the invention permits a host organism immunized with the resulting conjugate to generate antibodies specific for the conjugated peptide. Carriers include red blood cells, bacteriophages, proteins, or synthetic particles such as agarose beads. Preferably, carriers are proteins, such as serum albumin, gamma-globulin, keyhole limpet hemocyanin, thyroglobulin, ovalbumin, fibrinogen, or the like.

Peptides of the invention are synthesized by standard techniques, e.g. Stewart and Young, Solid Phase Peptide Synthesis, 2nd Ed. (Pierce Chemical Company, Rockford, Ill., 1984). Preferably, a commercial peptide synthesizer is used, e.g. Applied Biosystems, Inc. (Foster City, Calif.) model 430A. Peptides of the invention are assembled by solid phase synthesis on a cross-linked polystyrene support starting from the carboxyl terminal residue and adding amino acids in a stepwise fashion until the entire peptide has been formed. The following references are guides to the chemistry employed during synthesis: Merrifield, J. Amer. Chem. Soc., Vol. 85, pg. 2149 (1963); Kent et al., pg 185, in Peptides 1984, Ragnarsson, Ed. (Almquist and Weksell, Stockholm, 1984); Kent et al., pg. 217 in Peptide Chemistry 84, Izumiya, Ed. (Protein Research Foundation, B. H. Osaka, 1985); Merrifield, Science, Vol. 232, pgs. 341–347 (1986); Kent, Ann. Rev. Biochem., Vol. 57, pgs. 957–989 (1988), and references cited in these latter two references.

In solid state synthesis it is most important to eliminate synthesis by-products, which are primarily termination, deletion, or modification peptides. Most side reactions can be eliminated or minimized by use of clean, well characterized resins, clean amino acid derivatives, clean solvents, and the selection of proper coupling and cleavage methods and reaction conditions, e.g. Barany and Merrifield, The Peptides, Cross and Meienhofer, Eds., Vol. 2, pgs 1–284 (Academic Press, New York, 1979). It is important to monitor coupling reactions to determine that they proceed to completion so that deletion peptides missing one or more residues will be avoided. The quantitative ninhydrin reaction is useful for that purpose, Sarin et al. Anal. Biochem, Vol. 117, pg 147 (1981). Na-t-butyloxycarbonyl (t-Boc)—amino acids are used with appropriate side chain protecting groups stable to the conditions of chain assembly but labile to strong acids. After assembly of the protected peptide chain, the protecting groups are removed and the peptide anchoring bond is cleaved by the use of low then high concentrations of anhydrous hydrogen fluoride in the presence of a thioester scavenger, Tam et al., J. Amer. Chem. Soc., Vol. 105, pg. 6442 (1983). Side chain protecting groups used are Asp (OBzl), Glu(OBzl), Scr(Bzl), Thr(Bzl), Lys(Cl-Z), Tyr(Br-Z), Arg(NGTos), Cys(4-MeBzl), and His(ImDNP). (Bzl, benzyl; Tos toluene sulfoxyl; DNP, dinitrophenyl; Im, imidazole; Z, benzyloxgycarbonyl). The remaining amino acids have no side chain protecting groups. For each cycle the tBoc Na protected peptide-resin is exposed to 65 percent trifluoroacetic acid (from Eastman Kodak) (distilled before use) in dichloromethane (DCM), (Mallenckrodt): first for 1 minute then for 13 minutes to remove the Na-protecting group. The peptide-resin is washed in DCM, neutralized twice with 10 percent diisopropylethylamine (DIEA) (Aldrich) in dimethylformamide (DMF) (Applied Biosystems), for 1 minute each. Neutralization is followed by washing with DMF. Coupling is performed with the symmetric anhydride of the amino acid in DMF for 16 minutes. The symmetric anhydride is prepared on the synthesizer by dissolving 2 mmol of amino acid in 6 ml of DCM and adding 1 mmol of dicyclohexycarbodiimide (Aldrich) in 2 ml of DCM. After 5 minutes, the activated amino acid is transferred to a separate vessel and the DCM is evaporated by purging with a continuous stream of nitrogen gas. The DCM is replaced by DMF (6 ml total) at various stages during the purging. After the first coupling, the peptide-resin is washed with DCM, 10 percent DIEA in DCM, and then with DCM. For recoupling, the same amino acid and the activating agent, dicyclohexylcarbodiimide, are transferred sequentially to the reaction vessel. After activation in situ and coupling for 10 minutes, sufficient DMF is added to make a 50 percent DMF-DCM mixture, and the coupling is continued for 15 minutes. Arginine is coupled as a hydroxybenzotriazole (Aldrich) ester in DMF for 60 minutes and then recoupled in the same manner as the other amino acids. Asparagine and glutamine are coupled twice as hydroxybenzotriazole esters in DMF, 40 minutes for each coupling. For all residues, the resin is washed after the second coupling and a sample is automatically taken for monitoring residual uncoupled α-amine by quantitative ninhydrin reaction, Sarin et al. (cited above).

The general technique of linking synthetic peptides to a carrier is described in several references, e.g. Walter and Doolittle, "Antibodies Against Synthetic Peptides," in Setlow et al., eds., Genetic Engineering, Vol. 5, pgs. 61–91 (Plenum Press, N.Y., 1983); Green et al. Cell, Vol. 28, pgs. 477–487 (1982); Lerner et al., Proc. Natl. Acad. Sci., Vol. 78, pgs. 3403–3407 (1981); Shimizu et al., U.S. Pat. No. 4,474,754; and Ganfield et al., U.S. Pat. No. 4,311,639. Accordingly, these references are incorporated by reference.

Also, techniques employed to link haptens to carriers are essentially the same as the above-referenced techniques, e.g. chapter 20 in Tijsseu Practice and Theory of Enzyme Immunoassays (Elsevier, N.Y., 1985). The four most commonly used schemes for attaching a peptide to a carrier are (1) glutaraldehyde for amino coupling, e.g. as disclosed by Kagan and Glick, in Jaffe and Behrman, eds. Methods of Hormone Radioimmunoassay, pgs. 328–329 (Academic Press, N.Y., 1979), and Walter et al. Proc. Natl. Acad. Sci., Vol. 77, pgs. 5197–5200 (1980); (2) water-soluble carbodiimides for carboxyl to amino coupling, e.g. as disclosed by Hoare et al., J. Biol. Chem., Vol. 242, pgs. 2447–2453 (1967); (3) bis-diazobenzidine (DBD) for tyrosine to tyrosine sidechain coupling, e.g. as disclosed by Bassiri et al., pgs. 46–47, in Jaffe and Behrman, eds. (cited above), and Walter et al. (cited above); and (4) maleimidobenzoyl-N-hydroxysuccinimide ester (MBS) for coupling cysteine (or other sulfhydryls) to amino groups, e.g. as disclosed by Kitagawa et al., J. Biochem. (Tokyo), Vol. 79, pgs. 233–239 (1976), and Lerner et al. (cited above). A general rule for selecting an appropriate method for coupling a given peptide to a protein carrier can be stated as follows: the group involved in attachment should occur only once in the sequence, preferably at the appropriate end of the segment. For example, BDB should not be used if a tyrosine residue occurs in the main part of a sequence chosen for its potentially antigenic character. Similarly, centrally located lysines rule out the glutaraldehyde method, and the occurrences of aspartic and glutamic acids frequently exclude the carbodiimide approach. On the other hand, suitable residues can be positioned at either end of chosen sequence segment as attachment sites, whether or not they occur in the "native" protein sequence. Internal segments, unlike the amino and carboxy termini, will differ significantly at the "unattached end" from the same sequence as it is found in the native protein where the polypeptide backbone is continuous. The problem can be remedied, to a degree, by acetylating the α-amino group and then attaching the peptide by way of its carboxy terminus. The coupling efficiency to the carrier protein is conveniently measured by using a radioactively labeled peptide, prepared either by using a radioactive amino acid for one step of the synthesis or by labeling the completed peptide by the iodination of a tyrosine residue. The presence of tyrosine in the peptide also allows one to set up a sensitive radioimmune assay, if desirable. Therefore, tyrosine can be introduced as a terminal residue if it is not part of the peptide sequence defined by the native polypeptide.

Preferred carriers are proteins, and preferred protein carriers include bovine serum albumin, myoglobulin, ovalbumin (OVA), keyhole limpet hemocyanin (KLH), or the like. Peptides can be linked to KLH through cysteines by MBS as disclosed by Liu et al., Biochemistry, Vol. 18, pgs. 690–697 (1979). The peptides are dissolved in phosphate-buffered saline (pH 7.5), 0.1 M sodium borate buffer (pH 9.0) or 1.0 M sodium acetate buffer (pH 4.0). The pH for the dissolution of the peptide is chosen to optimize peptide solubility. The content of free cysteine for soluble peptides is determined by Ellman's method, Ellman, Arch. Biochem. Biophys., Vol. 82, pg. 7077 (1959). For each peptide, 4 mg KLH in 0.25 ml of 10 mM sodium phosphate buffer (pH 7.2) is reacted with 0.7 mg MBS (dissolved in dimethyl formamide) and stirred for 30 min at room temperature. The MBS is added dropwise to ensure that the local concentration of formamide is not too high, as KLH is insoluble in >30% formamide. The reaction product, KLH-MBS, is then passed through Sephadex G-25 equilibrated with 50 mM sodium phosphate buffer (pH 6.0)

to remove free MBS, KLH recovery from peak fractions of the column eluate (monitored by OD280) is estimated to be approximately 80%. KLH-MBS is then reacted with 5 mg peptide dissolved 25 in 1 ml of the chosen buffer. The pH is adjusted to 7–7.5 and the reaction is stirred for 3 hr at room temperature. Coupling efficiency is monitored with radioactive peptide by dialysis of a sample of the conjugate against phosphate-buffered saline, and ranged from 8% to 60%. Once the peptide-carrier conjugate is available polyclonal or monoclonal antibodies are produced by standard techniques, e.g. as disclosed by Campbell, Monoclonal Antibody Technology (Elsevier, N.Y., 1984); Hurrell, ed. Monoclonal Hybridoma Antibodies: Techniques and Applications (CRC Press, Boca Raton, Fla., 1982); Schreier et al. Hybridoma Techniques (Cold Spring Harbor Laboratory, New York, 1980); U.S. Pat. No. 4,562,003; or the like. In particular, U.S. Pat. No. 4,562,003 is incorporated by reference.

Both polyclonal and monoclonal antibodies can be screened by ELISA. As in other solid phase immunoassays, the test is based on the tendency of macromolecules to adsorb nonspecifically to plastic. The irreversibility of this reaction, without loss of immunological activity, allows the formation of antigen-antibody complexes with a simple separation of such complexes from unbound material. To titrate antipeptide serum, peptide conjugated to a carrier different from that used in immunization is adsorbed to the wells of a 96-well microtiter plate. The adsorbed antigen is then allowed to react in the wells with dilutions of antipeptide serum. Unbound antibody is washed away, and the remaining antigen-antibody complexes are allowed to react with antibody specific for the IgG of the immunized animal. this second antibody is conjugated to an enzyme such as alkaline phosphatase. A visible colored reaction product produced when the enzyme substrate is added indicates which wells have bound antipeptide antibodies. The use of spectrophotometer readings allows better quantification of the amount of peptide-specific antibody bound. High-titer antisera yield a linear titration curve between $10^{-3}$ and $10^{-5}$ dilutions.

EXAMPLES

The following examples serve to illustrate the present invention. Selection of vectors and hosts as well as the concentration of reagents, temperatures, and the values of other variable parameters are only to exemplify application of the present invention and are not to be considered as limitations thereof.

Example I

Biological Activities of Mouse CSIF

Mouse CSIF-containing supernatants from the several T cell clones were obtained by incubating the T cell clones ($5 \times 10^6$ cells/ml) in serum free medium (RPMI 1640 lacking phenol red and containing 0.05 mM 2-mercaptoethanol and 20 mM HEPES) and concanavalin A (5 µg/ml) for 24 hours. The clones included cell lines, D9 described in U.S. Pat. No. 4,613,459, D10 (described below), MB2-1 described in Mosmann et al, J. Immunol., Vol. 136, pgs. 2348–2357 (1986), CDC25 and CDC35 described in Tony et al, J. Exp. Med., Vol. 161, pgs. 223- (1985), and M411-2 and M411-6. The T cell supernatants were assayed for their ability to suppress IFN-$\gamma$ synthesis in the cell line HDK-1, described in Cherwinski, et al, J. Exp. Med., Vol. 166, pgs. 1229–1244 (1987). Serial twofold dilutions of samples from each T cell clone were prepared in 96-well flat-bottomed microtiter trays in a volume of 0.05 ml. HDK-1 cells ($5 \times 10^4$ cells per well) along with irradiated (2500 R) syngeneic APCs (spleen cells at $5 \times 10^5$ cells per well) and antigen (keyhole limpet hemocyanin at 150 µg/ml) were added in a volume of 0.15 ml. 11B11 anti-IL-4 antibody (10 µg/ml), described in Ohara et, Nature, Vol. 315, pgs. 333–336 (1985), was added to samples suspected of containing IL-4. After incubation at 37° C. for 24 h, supernatants were collected and kept at 4° C. for periods of less than a week, or at −80° C. for longer periods. Levels of IFN-$\gamma$ were assayed by two site sandwich ELISA using a rat anti-mouse IFN-$\gamma$ monoclonal antibody, XMG1.2, and affinity-purified rabbit anti-mouse IFN-$\gamma$ antibody. FIG. 1 shows the degree of inhibition of IFN-$\gamma$ synthesis as percentage of control levels.

CSIF produced by D10 cells was partially purified and applied to two different T cell clones to examine the degree of cytokine synthesis inhibition as a function of CSIF concentration. The partially purified CSIF was prepared as follows: 1–2.5 L batches of concanavalin A-induced D10 supernatant were concentrated approximately 10-fold using Amicon YM-5 membranes (Amicon Corp., Danvers, Mass.), passed through a 5-ml mannose-conjugated agarose column (E-Y Laboratories, San Mateo, Calif.), then further concentrated another 3- to 5-fold, for a total concentration of 30–50 fold. This material was then further purified by two steps of high performance liquid chromatography: first over a hydroxylapatite-based column (Bio-Gel HPHT, Bio-Rad Laboratories, Richmond, Calif.) and then over a gel filtration column (TSK-G 3000 SW, 60 cm length, LKB Instruments, Gaithersburg, Md.). One such batch of partially purified CSIF was kept in aliquots at −80° C. and used as a standard of CSIF activity. When initially assayed, this preparation caused approximately 50% inhibition of IFN-$\gamma$ production at a dilution of 1/200 in an assay volume of 0.2 ml, and so a standard unit was defined by assigning a value of 1000 U/ml to the standard CSIF preparation. In each assay below, the CSIF activity in unknown samples was quantitated by comparing levels of inhibition of IFN-$\gamma$ synthesis by the unknown to that of the standard. The T cell clones that were assayed for inhibition of cytokine synthesis were HDK-1 (described above) and MD13-10, described in Cell. Immunol., Vol. 97, pgs. 357- (1986). For the assay of IL-3 and GM-CSF levels the partially purified CSIF was further treated by passing it over anti-IL-3 and anti-GM-CSF affinity columns. Antibodies in 0.1 M NaCl, 0.1 M HEPES, and 0.08 M $CaCl_2$ were coupled to Affi-Gel 10 (Bio-Rad) at 4° C. with gentle mixing for 4 hours. Each 1–2 ml column contained approximately 10 to 20 mg of coupled antibody.

As shown in the table below, IFN-$\gamma$ production was inhibited in both clones. The synthesis of the other cytokines, IL-2, lymphotoxin, IL-3, and GM-CSF was inhibited to a lesser degree or not at all in MD13-10 cells.

TABLE

| | | % of Control Synthesis Level | | |
|---|---|---|---|---|
| Cell Line | Cytokine | 14 U/ml | 42 U/ml | 125 U/ml |
| HDK-1 | IFN-g | 47.6 | 29.1 | 18.6 |
| | IL-2 | 71.7 | 59.6 | 40.4 |
| | lymphotoxin | 41.9 | 45.1 | 42.8 |
| | IL-3 | 63.9 | 52.6 | 38.4 |
| | GM-CSF | 86.9 | 79.1 | 66.8 |
| MD13-10 | IFN-g | 36.0 | 27.5 | 23.2 |
| | IL-2 | 88.2 | 109.3 | 96.0 |
| | IL-3 | 60.2 | 63.0 | 51.0 |
| | GM-CSF | 109.0 | 119.9 | 97.6 |

Example II

Construction of cDNA Library From D10 Cells and Isolation of Clone pcD(SRa)-F115

A cDNA library was constructed in the pcD(SRα) vector from mRNA extracted from D10 cells, described in Kaye et al, J. Exp. Med., Vol. 158, pgs. 836- (1983), in accordance with the method of Okayama and Berg, Mol. Cell. Biol. 2: 161–170 (1982) and 3: 280–289 (1983), also disclosed in U.S. Pat. No. 4,695,542, which is incorporated by reference. The pcD(SRα) vectors carrying cDNA inserts were amplified in E. coli. Plasmid DNA was extracted from pools of these randomly picked clones and used to transfect COS 7 monkey cells as described below. The supernatants of the COS 7 cultures were then tested for CSIF activity. COS cells were transfected as follows: One day prior to transfection, approximately $1.5 \times 10^6$ COS 7 monkey cells were seeded onto individual 100 mm plates in Dulbecco's modified Eagle medium (DME) containing 5% fetal calf serum (FCS) and 2 mM glutamine. To perform the transfection, COS 7 cells were removed from the dishes by incubation with trypsin, washed twice in serum-free DME, and suspended to $10^7$ cells/ml in serum-free DME. A 0.75 ml aliquot was mixed with 20 μg DNA and transferred to a sterile 0.4 cm electroporation cuvette. After 10 minutes, the cells were pulsed at 200 volts, 960 μF in a BioRad Gene Pulser unit. After another 10 minutes, the cells were removed from the cuvette and added to 20 ml of DME containing 5% FCS, 2 mM glutamine, penicillin, streptomycin, and gentamycin. The mixture was aliquoted to four 100 mm tissue culture dishes. After 12–24 hours at 37° C., 5% $CO_2$, the medium was replaced with similar medium containing only 1% FCS and the incubation continued for an additional 72 hours at 37° C., 5% $CO_2$, after which the medium was collected and assayed for CSIF activity. Subsequently, the sequence of the largest open reading frame of the cDNA insert of pcD(SRα)-F115 was determined as follows:

```
ATGCCTGGCT CAGCACTGCT ATGCTGCCTG CTCTTACTGA
GTGGCATGAG GATCAGCAGG GGCCAGTACA GCCGGGAAGA
CAATAACTGC ACCCACTTCC CAGTCGGCCA GAGCCACATG
CTCCTAGAGC TGCGGACTGC CTTCAGCCAG GTGAAGACTT
TCTTTCAAAC AAAGGACCAG CTGGACAACA TACTGCTAAC
CGACTCCTTA ATGCAGGACT TTAAGGGTTA CTTGGGTTGC
CAAGCCTTAT CGGAAATGAT CCAGTTTTAC CTGGTAGAAG
TGATGCCCCA GGCAGAGAAG CATGGCCCAG AAATCAAGGA
GCATTTGAAT TCCCTGGGTG AGAAGCTGAA GACCCTCAGG
ATGCGGCTGA GGCGCTGTCA TCGATTTCTC CCCTGTGAAA
ATAAGAGCAA GGCAGTGGAG CAGGTGAAGA GTGATTTTAA
TAAGCTCCAA GACCAAGGTG TCTACAAGGC CATGAATGAA
TTTGACATCT TCATCAACTG CATAGAAGCA TACATGATGA
TCAAAATGAA AAGCTAA
``` and the amino acid sequence of the mature mouse CSIF protein determined by the Heijne algorthm is as follows:

```
QYSREDNNCTHFPVGQSHMLLELRTAFSQVKTFFQTKDQLDNILLTD
SLMQDFKGYLGCQALSEMIQFYLVEVMPQAEKHGPEIKEHLNSLGE
KLKTLRMRLRRCHRFLPCENKSKAVEQVKSDFNKLQDQGVYKAM
NEFDIFINCIEAYMMIKMKS
```

Example III

Screening cDNA Libraries for Human CSTF Using Probes Derived From pcD(SRα)-F115; Isolation of pH5C and pH15C A cDNA library constructed in pcD(SRα) from mRNA extracted from a human T cell clone was screened with a collection of 70-mer oligonucleotides whose sequences were complementary to the coding and noncoding strands of the fragment of the mouse CSIF gene encoding mature CSIF. Standard hybridization protocols were used, e.g. bacterial colonies grown on 150 mm petri dishes were transferred to GeneScreen membranes, treated with the radioactively labeled oligonucleotide probes, washed, then exposed to X-ray film. The probes were hybridized under low stringency conditions for the length of the probes: prehybridization consisted of incubation of the target nucleic acids in 5×SET (20×SET is 3 M NaCl+0.4 Tris-Cl (pH 7.8)+20 mM EDTA) at 60° C., followed by hybridization under the same conditions, and washing in 5×SET at 50° C. Two clones carrying plasmids pH5C and pH15C were identified. Both plasmids expressed proteins in COS 7 cells that were capable of inhibiting IFN-$\gamma$ synthesis in PHA-stimulated human PBLs. The cDNA insert of pH15C is illustrated in FIG. 4, and the nucleotide sequence of its largest open reading frame is given below:

```
5'- ATGCACAGCT CAGCACTGCT CTGTTGCCTG GTCCTCCTGA-
    CTGGGGTGAG GGCCAGCCCA GGCCAGGGCA CCCAGTCTGA-
    GAACAGCTGC ACCCACTTCC CAGGCAACCT GCCTAACATG-
    CTTCGAGATC TCCGAGATGC CTTCAGCAGA GTGAAGACTT-
    TCTTTCAAAT GAAGGATCAG CTGGACAACT TGTTGTTAAA-
    GGAGTCCTTG CTGGAGGACT TTAAGGGTTA CCTGGGTTGC-
    CAAGCCTTGT CTGAGATGAT CCAGTTTTAC CTGGAGGAGG-
    TGATGCCCCA AGCTGAGAAC CAAGACCCAG ACATCAAGGC-
    GCATGTGAAC TCCCTGGGGG AGAACCTGAA GACCCTCAGG-
    CTGAGGCTAC GGCGCTGTCA TCGATTTCTT CCCTGTGAAA-
    ACAAGAGCAA GGCCGTGGAG CAGGTGAAGA ATGCCTTTAA-
    TAAGCTCCAA GAGAAAGGCA TCTACAAAGC CATGAGTGAG-
    TTTGACATCT TCATCAACTA CATAGAAGCC TACATGACAA-
    TGAAGATACG AAACTGA-3'
```

Example IV

Monoclonal Antibodies Specific for CSIF

A male Lewis rat is immunized with semi-purified preparations of COS 7-cell expressed human CSIF. The rat is first immunized with approximately 50 μg of human CSIF in Freund's Complete Adjuvant, and boosted twice with the same amount of material in Freund's Incomplete Adjuvant.

Test bleeds are taken. The animal is given a final boost of 25 µg in phosphate-buffered saline, and four days later the spleen is obtained for fusion.

Approximately $3\times10^8$ rat splenocytes are fused with an equal number of P3X63-AG8.653 mouse myeloma cells (available from the ATCC under accession number CRL 1580). 3840 microtiter plate wells are seeded at $5.7\times10^4$ parental myeloma cells per well. Standard protocols for the fusion and subsequent culturing of hybrids are followed, e.g. as described by Chretien et al, J. Immunol. Meth., Vol. 117, pgs. 67–81 (1989). 12 days after fusion supernatants are harvested and screened by indirect ELISA on PVC plates coated with COS 7-produced human CSIF. Hybridoma JES3-19F1.1.1 was identified in this manner and deposited with the American Type Culture Collection under accession number HB10487.

Hybridomas producing blocking antibodies are selected from the initially screened hybridomas by their ability to produce antibodies that counteract the CSIF-induced inhibition of IFN-$\gamma$ synthesis in PHA-stimulated human PBLs.

Example V

Expression of Human CSIF in a Bacterial Host

A synthetic human CSIF gene is assembled from a plurality of chemically synthesized double stranded DNA fragments to form an expression vector designated TAC-RBS-hCSIF. Cloning and expression are carried out in a standard bacterial system, for example E. coli K-12 strain JM101, JM103, or the like, described by Viera and Messing, in Gene, Vol. 19, pgs. 259–268 (1982). Restriction endonuclease digestions and ligase reactions are performed using standard protocols, e.g. Maniatis et al., Molecular Cloning: A Laboratory Manual (Cold Spring Harbor Laboratory, New York, 1982).

The alkaline method (Maniatis et al., cited above) is used for small scale plasmid preparations. For large scale preparations a modification of the alkaline method is used in which an equal volume of isopropanol is used to precipitate nucleic acids from the cleared lysate. Precipitation with cold 2.5 M ammonium acetate is used to remove RNA prior to cesium chloride equilibrium density centrifugation and detection with ethidium bromide.

For filter hybridizations Whatman 540 filter circles are used to lift colonies which are then lysed and fixed by successive treatments with 0.5M NaOH, 1.5M NaCl; 1M Tris.HCl pH8.0, 1.5M NaCl (2 min each); and heating at 80° C. 25 (30 min). Hybridizations are in 6×SSPE, 20% formamide, 0.1% sodium dodecylsulphate (SDS), 100 mg/ml E. coli tRNA, 100 mg/ml Coomassie Brilliant Blue G-250 (Bio-Rad) at 42° C. for 6 hrs using $^{32}$P-labelled (kinased) synthetic DNAs. (20×SSPE is prepared by dissolving 174 g of NaCl, 27.6 g of $NaH_2PO_4 9H_2O$, and 7.4 g of EDTA in 800 ml of H2O. pH is adjusted to 7.4 with NaOH, volume is adjusted to 1 liter, and sterilized by autoclaving). Filters are washed twice (15 min, room temperature) with 1×SSPE, 0.1% SDS. After autoradiography (Fuji RX film), positive colonies are located by aligning the regrown colonies with the blue-stained colonies on the filters. DNA is sequenced by the dideoxy method, Sanger et al. Proc. Natl. Acad. Sci., Vol. 74, pg. 5463 (1977). Templates for the dideoxy reactions are either single stranded DNAs of relevant regions recloned into M13 mp vectors, e.g. Messing et al. Nucleic Acids Res., Vol. 9, pg. 309 (1981), or double-stranded DNA prepared by the minialkaline method and denatured with 0.2M NaOH (5 min, room temperature) and precipitated from 0.2M NaOH, 1.43M ammonium acetate by the addition of 2 volumes of ethanol. DNA is synthesized by phosphoramidite chemistry using Applied Biosystems 380A synthesizers. Synthesis, deprotection, cleavage and purification (7M urea PAGE, elution, DEAE-cellulose chromatography) are done as described in the 380A synthesizer manual.

Complementary strands of synthetic DNAs to be cloned (400 ng each) are mixed and phosphorylated with polynucleotide kinase in a reaction volume of 50 ml. This DNA is ligated with 1 mg of vector DNA digested with appropriate restriction enzymes, and ligations are in a volume of 50 ml at room temperature for 4 to 12 hours. Conditions for phosphorylation, restriction enzyme digestions, polymerase reactions, and ligation have been described (Maniatis et al., cited above). Colonies are scored for lacZ+ (when desired) by plating on L agar supplemented with ampicillin, isopropyl-1-thio-beta-D-galactoside (IPTG) (0.4 mM) and 5-bromo-4-chloro-3-indolyl-beta-D-galactopyranoside (x-gal) (40 mg/ml).

Figure 3:
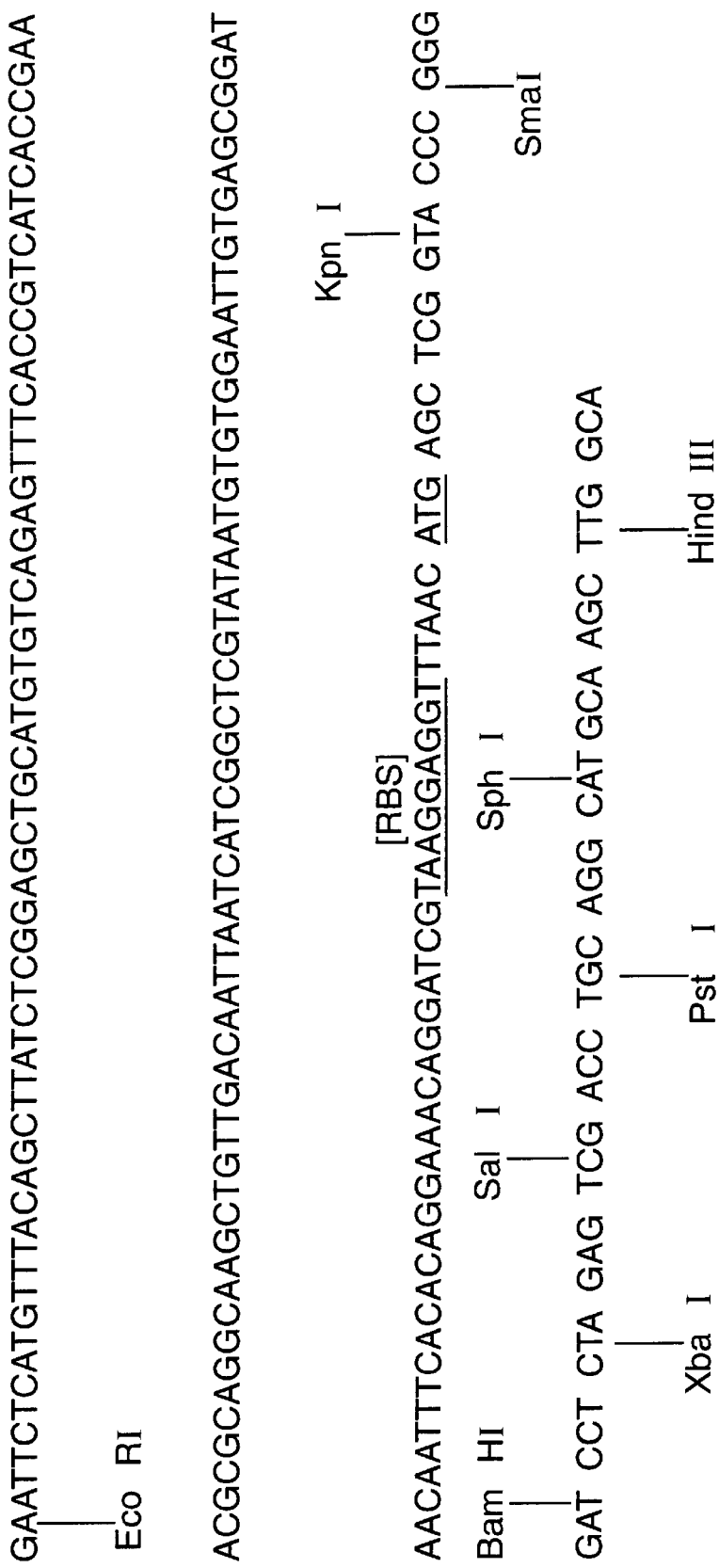
FIG. 3 illustrates the RBS-ATG-polylinker region of plasmid TAC-RBS-hCSIF.

The TAC-RBS vector is constructed by filling-in with DNA polymerase the single BamHI site of the tacP-bearing plasmid pDR540 (Pharmacia). This is then ligated to unphosphorylated synthetic oligonucleotides (Pharmacia) which form a double-stranded fragment encoding a consensus ribosome binding site (RBS, GTAAGGAGGTTTAAC). After ligation, the mixture is phosphorylated and religated with the SstI linker ATGAGCTCAT. This complex was then cleaved with SstI and EcoRI, and the 173 bp fragment isolated via polyacrylamide gel electrophoresis (PAGE) and cloned into EcoRI-SstI restricted pUC19 (Pharmacia) (as described below). The sequence of the RBS-ATG-polylinker regions of the final construction (called TAC-RBS) is shown in FIG. 3.

The synthetic CSIF gene is assembled into a pUC19 plasmid in eight steps. At each step inserts free of deletions and/or inserts can be detected after cloning by maintaining the lacZ(a) gene of pUC19 in frame with the ATG start codon inserted in step 1. Clones containing deletion and/or insertion changes can be filtered out by scoring for blue colonies on L-ampicillin plates containing x-gal and IPTG. Alternatively, at each step sequences of inserts can be readily confirmed using a universal sequencing primer on small scale plasmid DNA preparations, e.g. available from Boehringer Mannheim.

In step 1 the TAC-RBS vector is digested with SstI, treated with T4 DNA polymerase (whose 3' exonuclease activity digests the 3' protruding strands of the SstI cuts to form blunt end fragments), and after deactivation of T4 DNA polymerase, treated with EcoRI to form a 173 base pair (bp) fragment containing the TAC-RBS region and having a blunt end at the ATG start codon and the EcoRI cut at the opposite end. Finally, the 173 bp TAC-RBS fragment is isolated.

In step 2 the isolated TAC-RBS fragment of step 1 is mixed with EcoRI/KpnI digested plasmid pUC19 and synthetic fragment 1A/B which, as shown below, has a blunt end at its upstream terminus and a staggered end corresponding to an KpnI cut at its downstream terminus. This KpnI end is adjacent to and downstream of a BstEII site. The fragments are ligated to form the pUC19 of step 2.

In step 3 synthetic fragment 2A/B and 3A/B (shown below) are mixed with BstEII/SmaI digested pUC19 of step 2 (after amplification and purification) and ligated to form pUC19 of step 3. Note that the downstream terminus of fragment 3A/B contains extra bases which form the SmaI blunt end. These extra bases are cleaved in step 4. Also fragments 2A/B and 3A/B have complementary 9 residue single stranded ends which anneal upon mixture, leaving the upstream BstEII cut of 2A/B and the downstream blunt end of 3A/B to ligate to the pUC19.

In step 4 AflII/XbaI digested pUC19 of step 3 (after amplification and purification) is repurified, mixed with synthetic fragment 4A/B (shown below), and ligated to form pUC19 of step 4.

In step 5 XbaI/SalI digested pUC19 of step 4 (after amplification and purification) is mixed with synthetic fragment 5A/B (shown below) and ligated to form the pUC19 of step 5. Note that the SalI staggered end of fragment 5A/B is eliminated by digestion with HpaI in step 6.

In step 6 HpaIPstI digested pUC19 of step 5 (after amplification and purification) is mixed with synthetic fragment 6A/B (shown below) and ligated to form the pUC19 of step 6.

In step 7 ClaI/SphI digested pUC19 of step 6 (after amplification and purification) is mixed with synthetic fragment 7A/B (shown below) and ligated to form the pUC19 of step 7.

In step 8 MluI/HindIII digested pUC19 of step 7 (after amplification and purification) is mixed with synthetic fragments 8A/B and 9A/B and ligated to form the final construction. The final construction is inserted into *E. coli* K-12 strain JM101, e.g. available from the ATCC under accession number 33876, by standard techniques. After culturing, protein is extracted from the JM101 cells and dilutions of the extracts are tested for biological activity.

```
AGCCCAGGCC AGGGCACCCA GTCTGAGAAC AGCTGCACCC ACTTC-    Fragment 1A/B
TCGGGTCCGG TCCCGTGGGT CAGACTCTTG TCGACGTGGG TGAAG- CCAGGtAACC ggtac
GGTCCaTTGG c GtAACCTGCC TAACATGCTT CGAGATCTCC GAGATGCCTT CAGCA-    Fragment 2A/B
     GACGG ATTGTACGAA GCTCTAGAGG CTCTACGGAA GTCGT-

GAGTGAAGACTTTCTTT
CTCACTTC

CAAATGAAGG ATCAGCTGGA CAACTTGTTc TtAAG     Fragment 3A/B
TGAAAGAAA GTTTACTTCC TAGTCGACCT GTTGAACAAg AaTTC GAGTCCTTGC TGGAGGACTT TAAGGGTTAC CTGGGTTGCC AAGCC-    Fragment 4A B
CTCAGGAACG ACCTCCTGAA ATTCCCAATG GACCCAACGG TTCGG- TTGTCTGAGA TGATCCAGTT TTAt
AACAGACTCT ACTAGGTCAA AATaGAtC CTaGAGGAGG TGATGCCCCA AGCTGAGAAC CAAGACCCAG ACATC-    Fragment 5A B
GAtCTCCTCC ACTACGGGGT TCGACTCTTG GTTCTGGGTC TGTAG- AAGGCGCATG TtAACg
TTCCGCGTAC AaTTGcagct AACTCCCTGG GGGAGAACCT GAAGACCCTC AGGCTGAGGC TACGG-    Fragment 6A/B
TTGAGGGACC CCCTCTTGGA CTTCTGGGAG TCCGACTCCG ATGCC- CGCTGTCATC GATctgca
GCGACAGTAG CTAg CGATTTCTTC CCTGTCAAAA CAAGAGCAAG GCCGTGGAGC AGGTG-    Fragment 7A/B
 TAAAGAAG  GGACAGTTTT GTTCTCGTTC CGGCACCTCG TCCAC- AAGAAcGCgT gcatg
TTCTTgCGcA c CGCGTTTAAT AATAAGCTCC AAGACAAAGG CATCTACAAA GCCAT-    Fragment 8A/B
    AAATTA TTATTCGAGG TTCTGTTTCC GTAGATGTTT CGGTA-

GAGTGAGTTT GAC
CTCA

ATCTTCATCA ACTACATAGA AGCCTACATG ACAAT-     Fragment 9A/B
  CTCAAACTG TAGAAGTAGT TGATGTATCT TCGGATGTAC TGTTA- GAAGATACGA AACTGA
CTTCTATGCT TTGACTtcga (Lower case letters indicate that a base differs from that of the
native sequence at the same site)
```

Example VI

Antibodies Specific for the CENKSKAVE-Peptide 50 mg of ovalbumin (OVA) and 50 mg of myoglobulin (MYO) (e.g. available from Sigma) are each dissolved in 10 ml of 0.1 M sodium bicarbonate, and reacted with 1 ml of 0.12 iodoacetamide solution (88 mg of iodoacetamide dissolved in 4 ml 0.1 M sodium bicarbonate) for 1 hour at room temperature in a 15 ml Falcon tube (Falcon Plastics, Oxnard, Calif.), or the like. Each reaction mixture is dialyzed overnight against 4 liters of 0.1 M sodium bicarbonate at 4RC.

Separately, 10 mg of CENKSKAVE is dissolved in 2 ml of 0.1 M DTT (dithiotheitol) solution (containing 50 mM Tris and 2.5 mM EDTA at pH8) in a 4 ml tube, incubated at 37° C. overnight; and then applied to a GF05 gel-filtration column (1.5×26.5 cm) (LKB, Bromma, Sweden) and eluted with a peptide elution buffer consisting of 0.015 M acetic acid and 0.005 M beta-mercaptoethanol. Three fractions of about 3.5 ml each which contained the reduced peptide are identified by optical density at 206 nm, collected, pooled, frozen in dry ice, and lyophilized overnight. Meanwhile OVA and MYO are recovered from dialysis, and clarified by filtration through 0.45 micrometer filters. OVA and MYO are activated by mixing each with 380 microliters of N-hydroxysuccinimide ester of iodoacetic acid (NHIA) (disclosed by Rector et al., in J. Immunol. Meth., Vol. 24, pg. 321 (1978)) dissolved in tetrahydrofuran (THF) (5 mg/ml); stirring for 30 minutes at room temperature, and dialyzing overnight against 4 liters PBS (1.8 g $NaH_2PO_4$-$H_2O$, 7.2 g $Na_2HPO_4$-$H_2O$; and 34 g NaCl in 4 liters $H_2O$). Separately the lyophilized peptide is resuspended in 5 ml of borate reduction buffer (2 g $Na_2B_4O_7$-$10H_2O$, 17.4 g NaCl, and 336 mg EDTA-$Na_2$ in liter $H_2O$ with pH adjusted to 8.5 with concentrated HCl, deoxygenated under nitrogen for 15 minutes, after which 178 mg ascorbate is added). The dialyzed iodoacetylated OVA and MYO are recovered, separately mixed with equal volumes (preferably 2 ml) of borate reduction buffer containing the peptide, and incubated overnight at room temperature. The resulting conjugates are analyzed by SDS-PAGE (12.5% gel). The conjugate containing solution is diluted with PBS to 1 mg/ml, sterile filtered, and aliquotted to convenient volumes (e.g. 500 microliters) for immunizations, and/or stored at 4° C. Polyclonal anti-sera against the MYO conjugate is produced in both rats and rabbits (New Zealand White). The immunization schedule for rabbits is as follows: Initially (week 0) a 10 ml sample of serum is extracted as a control. One week later (week 1) 0.5 ml of peptide-carrier conjugate is mixed with 0.5 ml Freund's Complete Adjuvant and injected I.P. Three weeks later (week 4) a booster is given consisting of 0.5 ml peptide-carrier conjugate mixed with 0.5 ml Freund's Incomplete Adjuvant. The following week (week 5) an additional booster is given, again consisting of 0.5 ml peptide-carrier conjugate mixed with 0.5 ml Freund's Incomplete Adjuvant, followed by yet another identical booster the next week (week 6). On week 7, 20 ml of serum is bled from the animal. After separating out the cellular fraction the serum assayed for positive anti-CENKSKAVE titer by ELISA. Rat immunization proceed similarly except that the initial injection consists of 0.15 ml PBS and 0.1 ml peptide-carrier conjugate mixed with 0.75 ml Freund's Complete Adjuvant, boosters consisted of 0.15 ml PBS and 0.1 ml peptide-carrier conjugate mixed with 0.75 ml Freund's Incomplete Adjuvant, and only 2–3 ml of serum is bled from the rat. Again, a positive anti-CENKSKAVE reaction is detected by ELISA.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

Applicants have deposited separate cultures of E. coli MC1061 carrying pcD(SRα)-F115, pH5C, and pH15C, respectively, and hybridoma JES3-19F1.1.1 with the American Type Culture Collection, Rockville, Md., USA (ATCC), under accession numbers 68027, 68191, 68192 and HB10487, respectively. These deposits were made under conditions as provided under ATCC's agreement for Culture Deposit for Patent Purposes, which assures that the deposits will be made available to the US Commissioner of Patents and Trademarks pursuant to 35 USC 122 and 37 CFR 1.14, and will be made available to the public upon issue of a U.S. patent, which requires that the deposits be maintained. Availability of the deposited strain is not to be construed as a license to practice the invention in contravention of the rights granted under the authority of any government in accordance with its patent laws.

We claim:

1. A method of suppressing a humoral immune response in a human patient comprising administering to the patient an antibody against human cytokine synthesis inhibitory factor in an amount effective to block the biological activity (if human cytokine synthesis inhibitory factor.

2. The method of claim 1, wherein said cytokine synthesis inhibitory factor has the sequence:

```
SPGQGTQSEN SCTHFPGNLP NMLRDLRDAF SRVKTFFQMK

DQLDNLLLKE SLLEDFKGYL GCQALSEMIQ FYLEEVMPQA

ENQDPDIKAH VNSLGENLKT LRLRLRRCHR FLPCENKSKA

VEQVKNAFNK LQEKGIYKAM SEFDIFINYI EAYMTMKIRN.
```

3. The method of claim 1 wherein said antibody is a monoclonal antibody.

4. The method of claim 2 wherein said monoclonal antibody is produced by hybridoma JES3-19F1.1.1, or a subdone having all of the identifying characteristics of hybridoma JES3-10F1.1.1.

5. The method of claim 1 wherein said administering is parenteral.

6. The method of claim 1 wherein said antibody is administered at a dose of at least about 1 mg/kg per day.

7. A method of suppressing a humoral immune response in a human patient comprising administering to the patient a binding site from an antibody to said human cytokine synthesis inhibitory factor in an amount effective to block this biological activity of human cytokine synthesis inhibitory factor.

8. A method of suppressing a humoral immune response in a human patient comprising administering to the patient an antibody fragment against human cytokine synthesis inhibitory factor in an amount effective to block the biological activity of human cytokine synthesis inhibitory factor.

9. A method of suppressing a humoral immune response in a human patient comprising administering to the patient a binding composition specific for human cytokine synthesis inhibitory factor in an amount effective to block the biological activity of human cytokine synthesis inhibitory factor.

\* \* \* \* \*

UNITED STATES PATENT AND TRADEMARK OFFICE
CERTIFICATE OF CORRECTION

PATENT NO. : 6,207,154 B1  Page 1 of 1
DATED : March 27, 2001
INVENTOR(S) : Mosmann, et al.

It is certified that error appears in the above-identified patent and that said Letters Patent is hereby corrected as shown below:

<u>Column 26, claim 1,</u>
Line 25, delete "(if", and insert therefor -- of --.

Signed and Sealed this

Twenty-seventh Day of November, 2001

Attest:

*Nicholas P. Godici*

NICHOLAS P. GODICI
*Attesting Officer*   *Acting Director of the United States Patent and Trademark Office*